United States Patent
Selbekk

(10) Patent No.: US 10,324,063 B2
(45) Date of Patent: Jun. 18, 2019

(54) METHODS AND SYSTEMS FOR MEASURING PROPERTIES WITH ULTRASOUND

(71) Applicant: SINTEF TTO AS, Trondheim (NO)

(72) Inventor: Tormod Selbekk, Trondheim (NO)

(73) Assignee: Tomod Selbekk, Trondheim (NO)

( * ) Notice: Subject to any disclaimer, the term of this patent is extended or adjusted under 35 U.S.C. 154(b) by 141 days.

(21) Appl. No.: 15/121,451

(22) PCT Filed: Feb. 26, 2015

(86) PCT No.: PCT/GB2015/050560
§ 371 (c)(1),
(2) Date: Aug. 25, 2016

(87) PCT Pub. No.: WO2015/128656
PCT Pub. Date: Sep. 3, 2015

(65) Prior Publication Data
US 2016/0363561 A1 Dec. 15, 2016

(30) Foreign Application Priority Data

Feb. 26, 2014 (GB) .................................. 1403393.0

(51) Int. Cl.
*G01N 29/032* (2006.01)
*G01N 29/07* (2006.01)
(Continued)

(52) U.S. Cl.
CPC ......... *G01N 29/024* (2013.01); *G01N 29/032* (2013.01); *G01N 29/07* (2013.01);
(Continued)

(58) Field of Classification Search
CPC .... G01N 29/024; G01N 29/032; G01N 29/07; G01N 29/11; G01N 29/4472;
(Continued)

(56) References Cited

U.S. PATENT DOCUMENTS 4,357,944 A 11/1982 Mauser et al.
4,653,505 A 3/1987 Iinuma
(Continued)

FOREIGN PATENT DOCUMENTS

GB 2498519 A 7/2013
WO 01977704 A2 12/2001
(Continued)

OTHER PUBLICATIONS

Takenoshita M. et al.,"Detection of ultrasonic flowmeter beam incident angle for precise blood velocity measurements", Engineering in Medicine and Biology Society, pp. 994-995 (Oct. 1993).

*Primary Examiner* — Jacques M Saint Surin
(74) *Attorney, Agent, or Firm* — Browdy and Neimark, P.L.L.C.

(57) ABSTRACT

A method of measuring a property of a medium using ultrasound, comprising: transmitting one or more ultrasound pulses into the medium from one or more transmitters and receiving at least a first echo signal and a second echo signal from within the medium at one or more receivers, wherein the first and second echo signals correspond to first and second pulse transmission paths within the medium from the one or more sources to the one or more receivers, the second path being different from the first path; and using the characteristics of the first and second echo signals together with an estimate of the property of the medium and a geometrical relationship between the first and second transmission paths to calculate a revised estimate of said property of the medium. By using two different beam paths within the medium, the first and second echoes will have had slightly different interactions with the medium. For example the different paths may well have different lengths thus giving different amounts of interaction such as different amplitude or phase effects on the different pulses. By comparing the similarities and differences between the pulses, certain prop- (Continued)

erties of the medium can be discerned. Many different properties can be investigated using these principles. In particular, the speed of sound in a medium can be measured and the direction and magnitude of a flow or particle movement within the medium can be measured. An iterative process may be used.

24 Claims, 20 Drawing Sheets

(51) Int. Cl.
  *G01N 29/11* (2006.01)
  *G01N 29/44* (2006.01)
  *G01N 29/024* (2006.01)
(52) U.S. Cl.
  CPC ......... *G01N 29/11* (2013.01); *G01N 29/4472* (2013.01); *G01N 2291/011* (2013.01); *G01N 2291/02475* (2013.01); *G01N 2291/044* (2013.01); *G01N 2291/0421* (2013.01)
(58) Field of Classification Search
  CPC ... G01N 2291/02475; G01N 2291/044; G01N 2291/011; G01N 2291/0421
  USPC .......................................................... 73/597
  See application file for complete search history.

(56) References Cited

U.S. PATENT DOCUMENTS

| | | | | |
|---|---|---|---|---|
| 4,688,423 A * | 8/1987 | Orkosalo | ............... | G01N 29/07 |
| | | | | 310/334 |
| 5,918,281 A * | 6/1999 | Nabulsi | ..................... | G01F 1/10 |
| | | | | 73/597 |
| 6,423,006 B1 | 7/2002 | Banjanin | | |
| 6,634,233 B2 * | 10/2003 | He | ......... | G01N 29/07 |
| | | | | 73/597 |
| 6,680,688 B1 * | 1/2004 | Jiang | ...................... | G01S 11/16 |
| | | | | 340/435 |
| 6,883,376 B2 * | 4/2005 | He | ......... | G01B 17/02 |
| | | | | 73/597 |
| 2006/0100515 A1 | 5/2006 | Nakata | | |
| 2008/0011060 A1* | 1/2008 | Lynnworth | .......... | G01N 29/024 |
| | | | | 73/64.53 |
| 2009/0227870 A1 | 9/2009 | Kolkman et al. | | |

FOREIGN PATENT DOCUMENTS

WO  2008097479 A1  8/2008
WO  2012131340 A2  10/2012

* cited by examiner

Fig. 2(A)
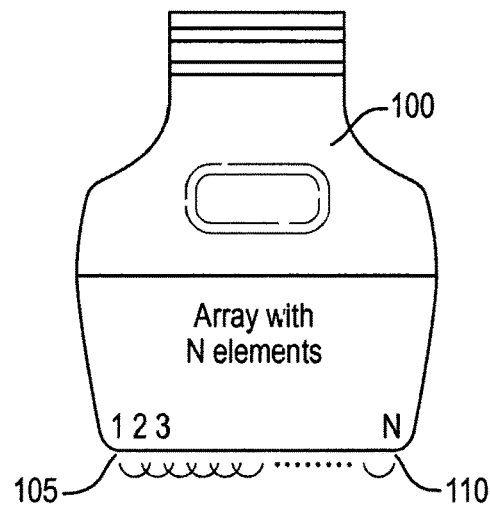
Fig. 2(B)
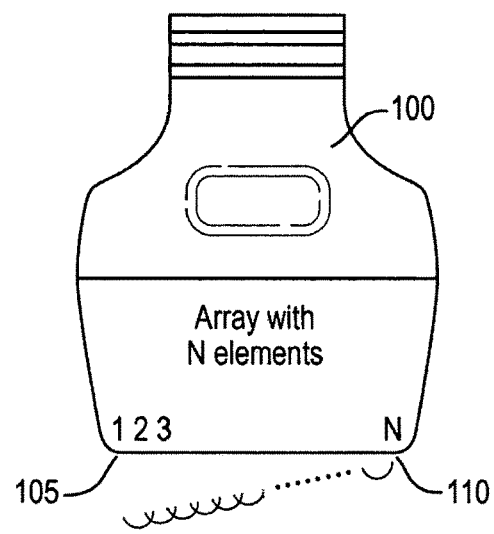

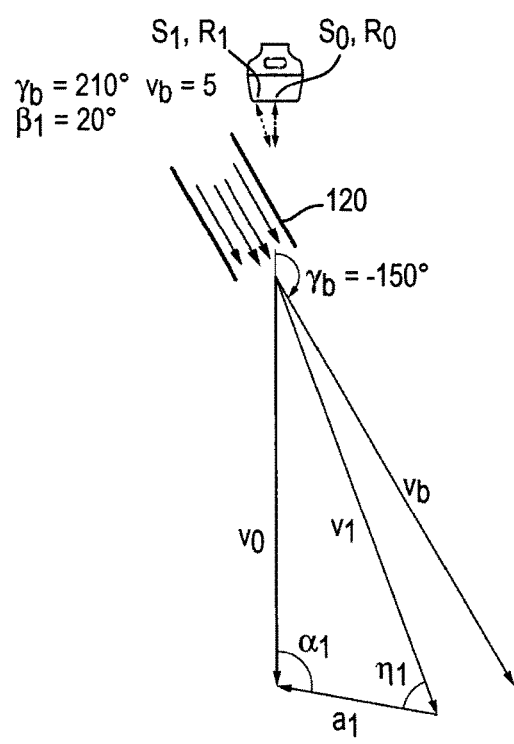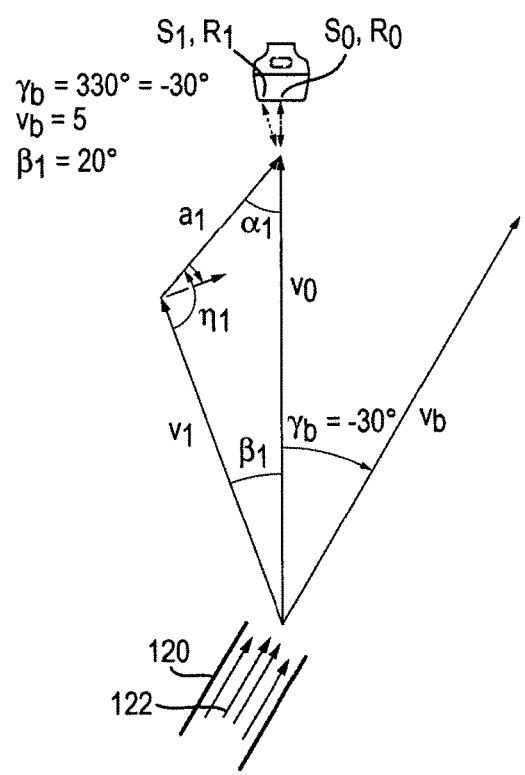

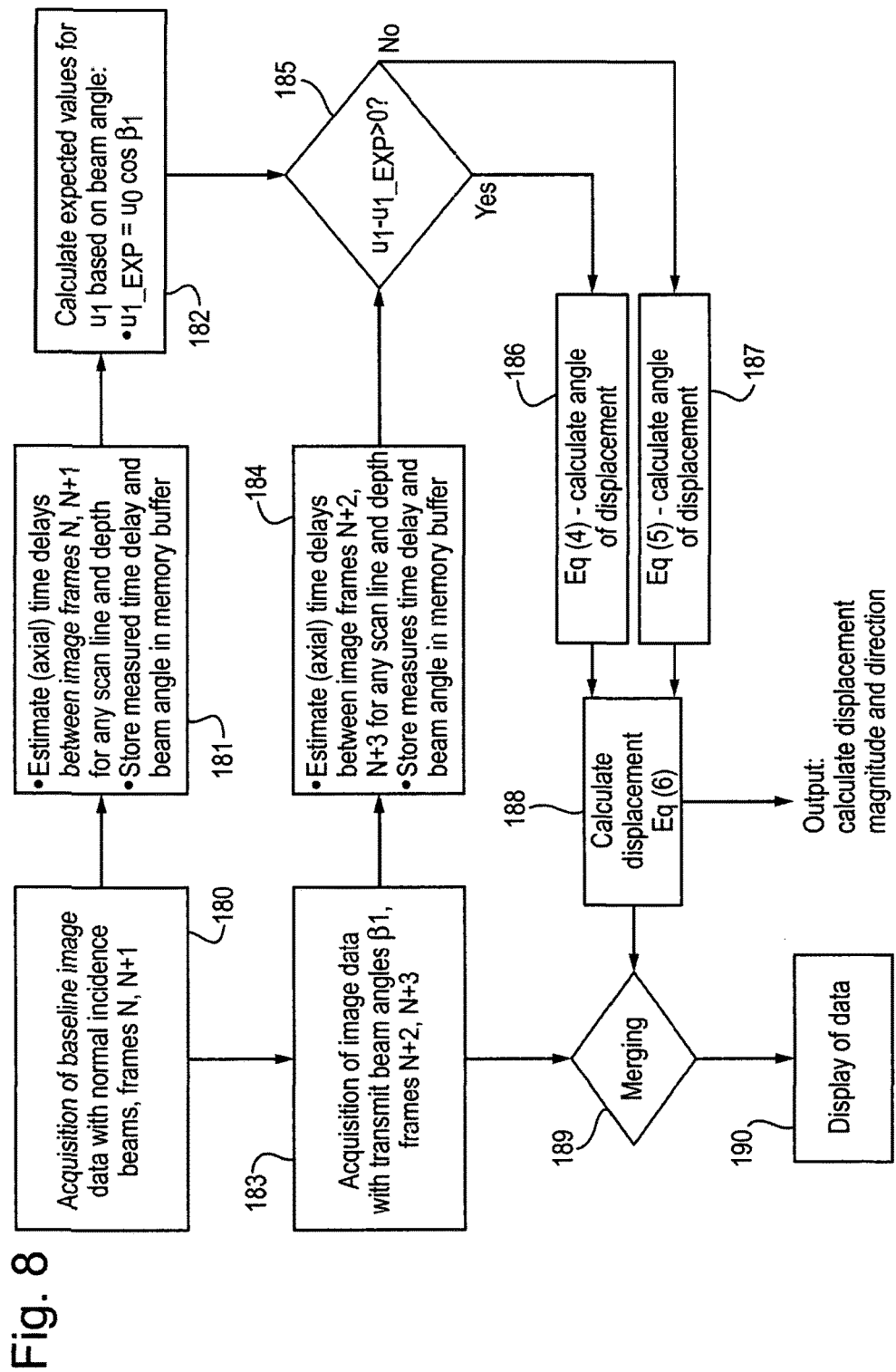

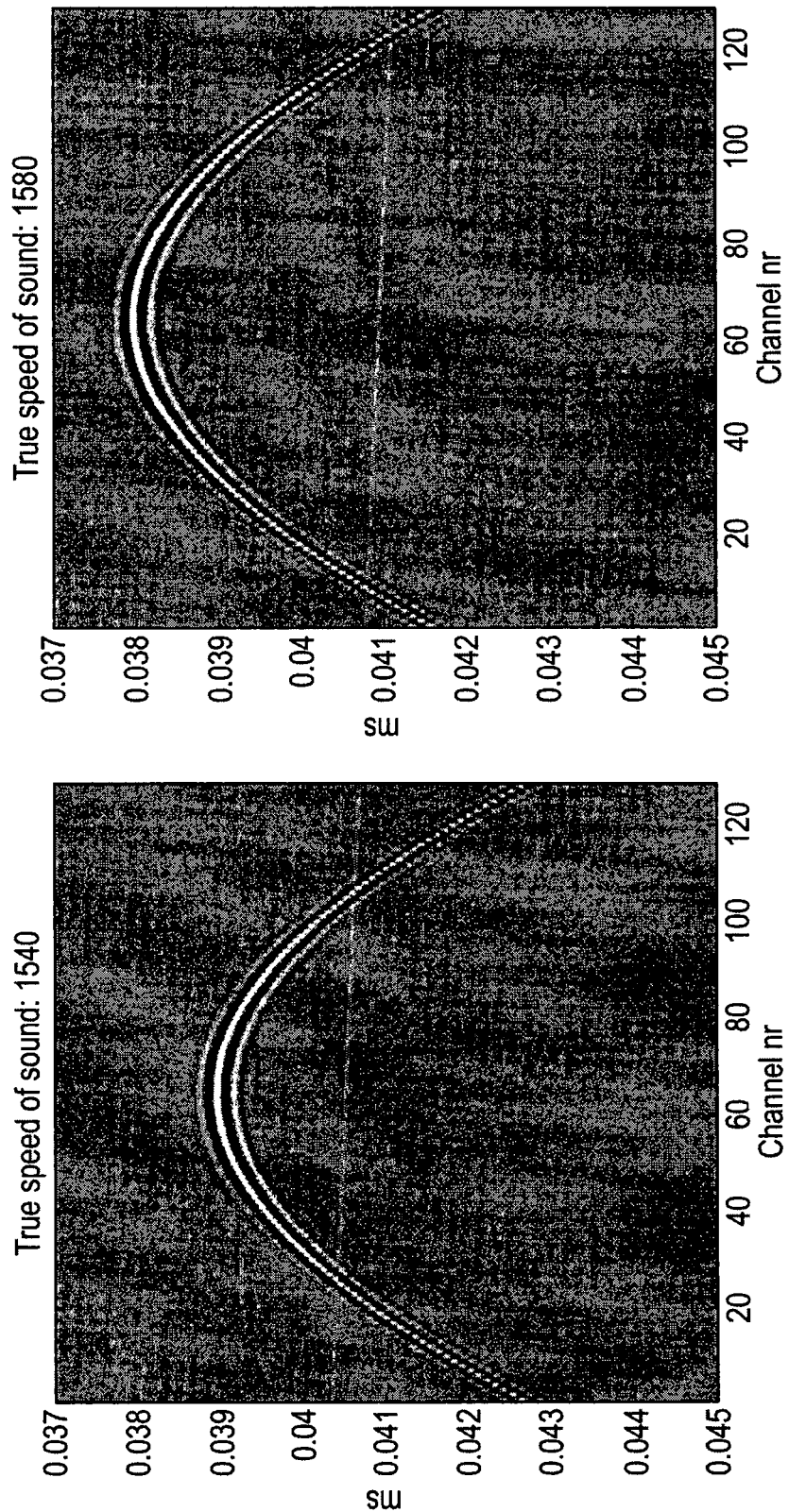

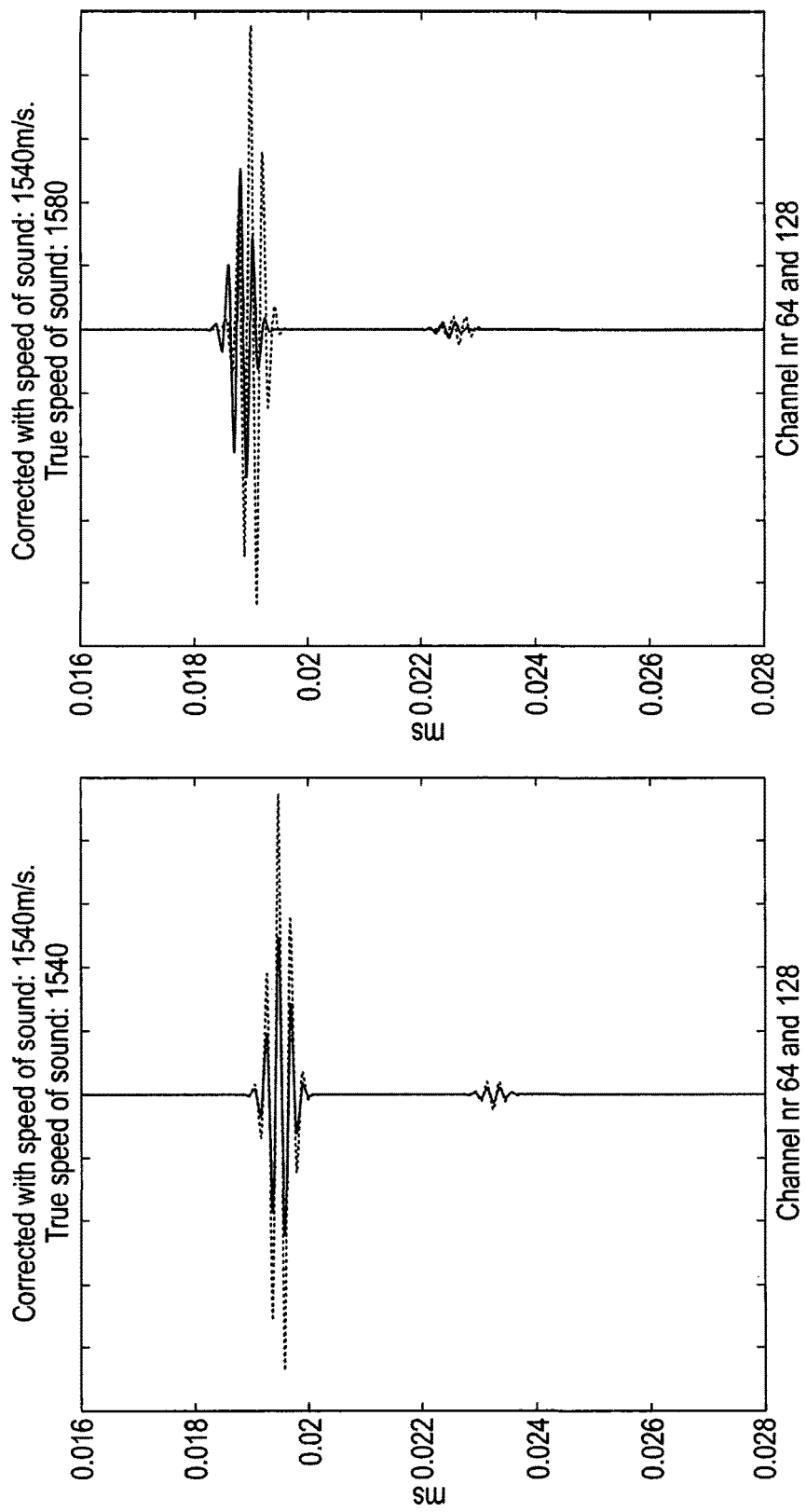
Fig. 16 (Cont I)

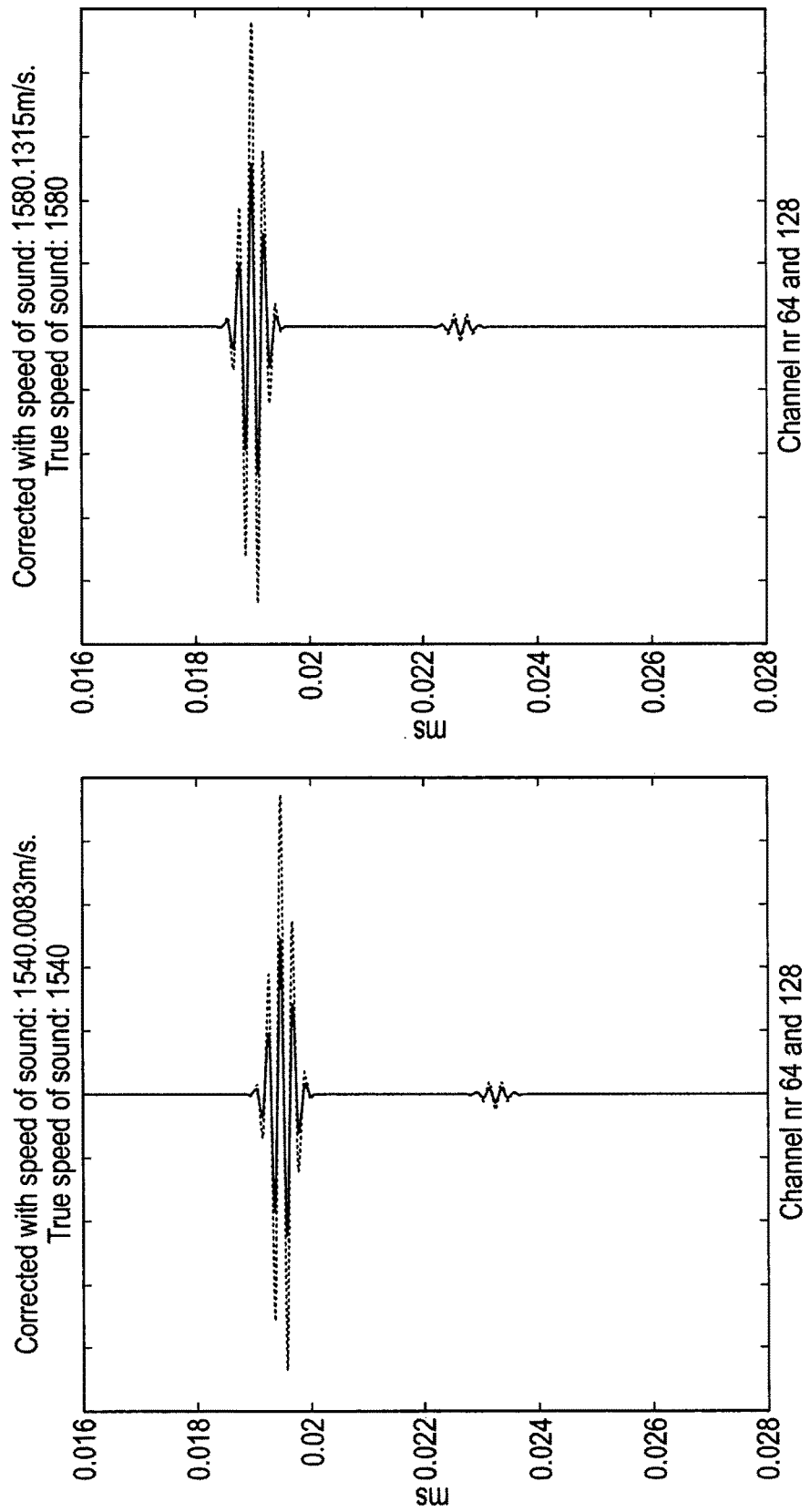
Fig. 16 (Cont II)

METHODS AND SYSTEMS FOR MEASURING PROPERTIES WITH ULTRASOUND

The invention relates to methods and systems for measuring the properties of a medium using ultrasound. In particularly preferred forms, the invention concerns a method for estimation of material properties or material behaviour in an investigated medium using acoustic waves by analysing the change in attributes like travel time, amplitude or frequency modulation of the acoustic wave, with different source-receiver locations and/or different beam angles and/or different beam propagation paths.

Sound is mechanical vibrations that propagate in a given medium. The medium may be fluids, gases, solids or plasma. In gases, fluids and plasma the sound travels as compressional waves (also called longitudinal waves) which means that all particles in the medium will move along, or parallel to, the direction of travel for the wave energy. In solids the sound may in addition also travel as transverse waves, in which particles vibrate in direction perpendicular to the direction of the wave energy.

Sound in the human audible range has frequencies between approximately 20 Hz to 20 000 Hz. Ultrasound is defined as sound with frequencies above 20 kHz. In medical imaging the ultrasound frequency range is typically between 2-40 MHz.

Ultrasound imaging is widely used in medical examination, and is used in various clinical fields. Ultrasound imaging is a pulse-echo technique. The generation of the ultrasound images is based upon transmission of a sound pulse and receiving of echoed events that have been reflected from tissue boundaries or scattered from smaller objects. In conventional scanners today, a narrow ultrasound beam is transmitted from the ultrasound transducer. When the transmitted pressure pulse meets a hindrance in the form of a boundary between different soft tissues, or scatter points within the tissue with different acoustic properties, some of the energy of the transmitted sound pulse is echoed back to the transducer. This process enables formation of ultrasound displays using various imaging modes such as brightness mode (B-mode), motion mode (M-mode), Doppler mode, elastography mode, and more. The ultrasound imaging can be performed with ultrasound scanners with scanner specific ultrasound transducers that emit and receive the sound. Although many references in the text below are to a 1D transducer, the transducers can in general be 1D transducers (generating 2D images), multi-row transducers and fully 2D transducers that may be capable of real-time 3D imaging (also known as 4D imaging).

The display of organs and anatomy can be performed by B-mode imaging. In the B-mode images the brightness of an image pixel is related to the strength of the reflected echo. The vertical position of each pixel with a given brightness indicates the time period from pulse transmission to echo receive, and the horizontal position indicates the lateral position of the acquired scan lines. The B-mode imaging is also referred to as 2D mode imaging as it produces a 2D cross sectional view of the body.

In ultrasound imaging the speed of sound c is assumed to be constant in the medium explored. This assumption is to some extent always violated in medical ultrasound imaging, as the speed of sound is known to vary in magnitude in different media. For example, the speed of sound is approx. 330 m/s in air and 1480 m/s in fresh water. In biological tissue the speed of sound varies from approx. 600 m/s in lung tissue, to ca. 4000 m/s in bone. Fat has a speed of sound of approximately 1460 m/s, liver 1555 m/s, and muscle approximately 1600 m/s. A standard setting in commercial medical ultrasound scanners is a constant speed of sound of 1540 m/s for soft biological tissue. This difference between the speed of sound in the scanner setting and the true speed of sound of the tissues may cause improper delineation of geometry, depth range errors and phase aberration. The latter phenomenon refers to defocusing of the ultrasound beam caused by distortions of the ultrasound wavefront due to differences in the speed of sound. Portions of the propagating wavefront will be advanced or retarded depending on the speed of sound, and this may cause distortions in the focusing and steering of the ultrasound beam. This may in turn lead to reduced resolution and contrast in the ultrasound images.

The estimation of time delays between image frames, i.e. local differences in travel time of reflected pulses between consecutive ultrasound image frames, is well established, and various methods have been described for the purpose of estimating tissue displacement and velocity. Examples of such methods are presented in a paper titled *An axial velocity estimator for ultra-sound blood flow imaging, based on a full evaluation of the Doppler equation by means of a two-dimensional autocorrelation approach* by Loupas et al. (1995), which describes among others the autocorrelator method, cross-correlator method and 2D autocorrelator method. Such methods can detect differences in travel time between two acquired image frames to an accuracy of the order of a fraction of the sampling period. By processing of Radio-Frequency ultrasound data it has been shown that it is possible to detect time shifts of a fraction of the sampling period.

Another inherent assumption in ultrasound imaging presently is that the absorption in the imaged medium is constant. This may not be the case, and therefore ultrasound scanners have TGC (time-gain-compensation) settings which can be adjusted manually so as to compensate for absorption with depth.

The amplitude of the ultrasound pulse will gradually decrease as it propagates in the tissue. The attenuation of a given medium is given by the attenuation coefficient α, which usually is expressed as a damping value in decibel per centimeter per MegaHertz [dB/(cm*MHz)].

The total attenuation can be estimated by the equation:

$$\text{Attenuation [dB]} = \alpha[\text{dB}/(\text{MHz}*\text{cm})] * l[\text{cm}] * f[\text{MHz}]$$

Wherein
α is the attenuation coefficient
l is the medium length (or propagating distance)
f is the frequency of the transmitted ultrasound wave Ultrasound technology may be used for estimation of blood flow velocity in blood vessels. The Doppler Mode is used for measuring and visualization of blood flow, based on the Doppler effect. The Doppler frequency shift $f_D$ for a signal with frequency $f_0$ being reflected from an object with velocity v propagating with an angle θ relative to the sound beam is provided by:

$$f_D = 2 f_0 \frac{v \cos\theta}{c}$$

The Doppler shift can be analysed along a single beam (sometimes referred to as spectral Doppler) or by providing a 2D image (e.g. colour flow imaging). The velocities estimated from the above equation may not represent the true blood flow velocity within the vessel, as the calculated velocity is dependent on the angle between the blood vessel and the ultrasound beam and this is not always accurately known. D. E. ROBINSON, F. CHEN and L. S. WILSON. MEASUREMENT OF VELOCITY OF PROPAGATION FROM ULTRASONIC PULSE-ECHO DATA. Ultrasound in Med. & Biol, 1983:8(4):413-420 proposes two technique for measuring the velocity in a medium. Firstly a direct calculation method relies on distances that are manually measured in the image in order to calculate a fractional velocity based on the distance between two echoes shown in the image. An iterative method is also proposed. In the iterative method, a range of velocities is tried, with successive iterations trying to minimise the distance between the two echoed events in the image. The velocity causing the most overlapping echoes is taken as the closest estimate.

Qu X, Azuma T, Liang J T, Nakajima Y. Average sound of speed estimation using speckle analysis of medical ultrasound data. Int J CARS, 2012:7:891-899 uses the imaged speckle pattern size to estimate the average speed of sound in the medium. The variation in speckle size is used to evaluate the focus quality as a misaligned focus will lead to larger speckle size. Focus quality is expressed by a normalized autocovariance function and a series of different velocities is tried with the aim of minimising the speckle size.

According to the invention there is provided a method of measuring properties of a medium using ultrasound, comprising: transmitting one or more ultrasound pulses into the medium from one or more transmitters and receiving at least a first echo and a second echo from within the medium at one or more receivers, wherein the first and second echoes have travelled along first and second paths within the medium from the one or more sources to the one or more receivers, the second path being different from the first path; and using the characteristics of the received first and second echoes to calculate properties of the medium.

By using two different beam paths within the medium, the first and second echoes will have had slightly different interactions with the medium. For example the different paths may well have different lengths thus giving different amounts of interaction such as different amplitude or phase effects on the different pulses. By comparing the similarities and differences between the pulses, certain properties of the medium can be discerned. Many different properties can be investigated using these principles.

In addition to the characteristics of the received echoes, the method may make use of known locations of source(s) and/or receiver(s) or known angles of the propagated waves (transmit and/or receive) with respect to a reference plane to calculate properties of the medium. These characteristics of the system setup form a geometrical relationship which can be used in the subsequent calculations. The geometrical relationship can include the physical relationship between the source(s) and receiver(s) and/or it can include the relationship of the transmission paths of the pulse(s) and echo(es) within the medium.

Viewed from another aspect, the invention provides a method of measuring a property of a medium using ultrasound, comprising: transmitting one or more ultrasound pulses into the medium from one or more transmitters and receiving at least a first echo signal and a second echo signal from within the medium at one or more receivers, wherein the first and second echo signals correspond to first and second pulse transmission paths within the medium from the one or more sources to the one or more receivers, the second path being different from the first path; and using the characteristics of the first and second echo signals together with an estimate of the property of the medium and a geometrical relationship between the first and second transmission paths to calculate a revised estimate of said property of the medium.

As discussed above, the geometrical relationship may comprise the distance between transmitters and receivers and/or the angles of the transmitted beams and/or other geometrical knowledge such as the known or estimated depth of a target scatterer, object or interface.

The calculating step may comprise: estimating the characteristics of the received second echo signal based on the characteristics of the received first echo signal, the estimate of the property of the medium and the geometrical relationship; and calculating the revised estimate based on the estimated characteristics of the received second echo signal and the measured characteristics of the received second echo signal.

The characteristics of the first and second echo signals may comprise the travel times of the first and second pulses respectively, and the property of the medium may comprise one of the following: speed of sound in the medium, attenuation in the medium.

The calculating step may comprise: estimating a feature of the second path based on the estimate of the property of the medium, the characteristics of the received first echo signal and the geometrical relationship; estimating the same feature of the second path based on the estimate of the property of the medium and the characteristics of the received second echo signal; and calculating the revised estimate based on a comparison of the two estimates of the feature of the second path. This provides an alternative and essentially equivalent way of performing the calculation described above.

The feature of the second path may be the path length of the second path and the property of the medium may comprise one of the following: speed of sound in the medium, attenuation in the medium.

The first and second echoes may originate from a single source pulse. Alternatively, the first and second echoes originate from two or more source pulses. Generally, transducers may be used in either a transmit mode or a receive mode and can thus be used (at different times) as both source and receiver. One part of a transducer array may act as a source while a different part of the transducer array acts as a receiver. A pulse sent from one source (which may be a number of transducers or transducer elements being a subset of a larger array) may generate echoes at more than one angle. Therefore different paths can be investigated from a single source by using two or more receivers at different locations. Similarly, a single receiver could be arranged to receive echoes from more than one source at different locations, again creating different pulse transmission paths within the medium.

The echo characteristics used in calculations may include one or more of: travel time, received amplitude, received phase, frequency spectrum, or any characteristic derived from these characteristics. This is not intended to be taken as an exhaustive list. Other characteristics may also be used.

The medium properties calculated from the echo characteristics may include one or more of: speed of sound in the medium, attenuation in the medium, flow or particle movement direction within the medium, displacement within the medium, strain within the medium, velocities within the medium, and angle or curvature of interfaces or bodies within the medium, or any characteristics derived from any of these properties.

Again, this is not intended to be taken as an exhaustive list. Other properties may also be used.

In some preferred embodiments the speed of sound in the medium is calculated from the difference in travel times along each of the first and second paths and the distances between source and receiver for each of the first and second paths. Taking two measurements of travel time along two different paths in the medium and knowing some (but not necessarily all) of the other geometry of the set up such as the depth of reflection, the separation distance of the source(s) and receiver(s) and/or the beam transmission/reception angles, an accurate speed of sound within the medium can be calculated. Measuring the speed of sound in the medium in this way can be used to improve imaging by improving the depth interpretation of received signals and more accurately portraying the received data in an image. Equally the measured speed of sound can improve quantitative measurements of other medium properties that rely on knowing accurate depths and/or speeds. Thus improved accuracy in such quantitative measurements can be achieved.

In some preferred embodiments the speed of sound in the medium is calculated from the difference in travel times along each of the first and second paths and the beam angles for each of the first and second paths.

The attenuation in the medium may be calculated based on the received amplitudes of the first and second echoes and the path lengths of the first and second echoes. In this way, the attenuation over two different paths within the medium can be compared and can be used to extract the attenuation coefficient of the medium in the region investigated.

A flow or particle movement direction within the medium may be calculated based on the angle between the two transmit directions and the velocities measured along the two paths. This technique has particular application in identifying and calculating properties of fluid flows within a medium where the angle of the flow is (or may be) at an angle to the transducer. For example when trying to monitor or measure blood (or other fluid) flow in a vessel within a human or animal body, the exact angle of the vessel to the body surface may not be known or it may not be possible to align the transducer with the flow due to other obstructions such as bones that inhibit the ultrasound signal. Taking measurements of fluid flow from different angles allows determination of the relative orientation of the vessel (or more precisely the flow) with respect to the transducers. In addition to calculating the direction of the vessel accurately, the maximum fluid velocity can be calculated accurately which is useful on its own, but also facilitates other measurements such as volume flow measurements.

In some preferred embodiments at least three echoes are received along three beam paths to provide three measurements of velocity and curve fitting and extrapolation or interpolation are used to find the direction of maximum velocity. With three (or more) measurements, a curve can be plotted which maps the measured velocities and which can be used to extrapolate (or interpolate) the position at which velocity is a maximum (which is normally expected to be in the direction of the vessel).

The inclination angle of a boundary within the medium with respect to the transducer surface may be calculated based on the difference in travel times along each of the first and second paths and the distances between source and receiver for each path. Multiple measurements in different regions of interest can be used to map curved surfaces and thereby to map boundaries accurately within the medium. For example this technique could be used to map the shape of organs within the body.

Although in many situations, the medium properties may be calculated directly from the measurements, there may be situations where those calculations are hindered or where the calculations are too complex for real time processing. Therefore in some embodiments the received echo characteristics may be compared with outputs from a theoretical model that models the medium so as to extract or calculate the model parameters that best match the received echo characteristics. Using a model allows a significant amount of processing to be performed in advance, thus reducing the processing required at the time of acquisition.

For example, in some preferred embodiments the model may provide expected time differences for a given reference speed of sound at various depths and various source locations and receiver locations. The model may provide an output as a function of its inputs. The model may comprise a lookup table that relates the input parameters to one or more expected characteristic values. The values in the lookup table may be derived from theoretical calculations. The values in the lookup table may be derived from empirical investigations.

There are significant benefits to the ability to obtain accurate measurements of the medium properties in a single region of interest. However, the ability to perform such measurements at the time of measurement (and in many cases in real time) allows multiple regions of interest to be investigated in a short period of time. Therefore the properties of the medium may be investigated at a plurality of regions of interest within the medium. In a basic form this allows a comparison of two areas within the medium to assess whether a property is essentially constant or varies through the medium. By extension to a greater number of regions of interest, the way that a property varies can be investigated and mapped in one, two or three dimensions within the medium. For example, the attenuation within a medium may not be constant, but could vary with depth. This would necessarily have an impact on other investigations which rely on measured receive amplitudes from reflections within such a region.

In some preferred embodiments the plurality of measurements forms a two or three dimensional grid of measurements.

In some preferred embodiments measurements of a characteristic of the medium at a shallow depth are taken into account in calculations relating to measurements of a characteristic at a deeper depth. This may be the case for example where the medium being investigated includes a number of distinct layers, each of which may have a slightly different value of a property. For example human or animal bodies comprise several different tissues through which ultrasound signals may have to pass when investigating some deeper objects of interest. The speed of sound and attenuation (for example) may vary slightly in the different layers. The signal reflected from the deepest layer will be affected by having passed through all shallower layers and therefore for accurate measurement and calculation those layers need to be investigated accurately too. By taking measurements at several regions of interest at different depths within the medium, each layer can be investigated and accurate property values can be determined for each layer and then taken into account for each deeper layer.

It should be noted that the property being calculated at the deepest depth may be the same property as is investigated at shallower depths or it may be a different property.

According to another aspect, the invention provides an ultrasound apparatus for measuring properties of a medium, comprising: one or more sources for transmitting ultrasound pulses into the medium; one or more receivers for receiving ultrasound pulses from the medium; and a processor arranged to: transmit one or more ultrasound pulses into the medium and receive at least first and second echoes from within the medium, wherein the first and second echoes have travelled along first and second paths within the medium from the at least one source to the at least one receiver, the second path being different from the first path; and calculate one or more properties of the medium using the characteristics of the first and second received echoes.

Viewed from another aspect, the invention provides an ultrasound apparatus for measuring a property of a medium, comprising: one or more sources for transmitting ultrasound pulses into the medium; one or more receivers for receiving ultrasound pulses from the medium; and a processor arranged to: transmit one or more ultrasound pulses into the medium and receive at least first and second echo signals from within the medium, wherein the first and second echo signals correspond to first and second pulse transmission paths within the medium from the at least one source to the at least one receiver, the second path being different from the first path; and use the characteristics of the first and second echo signals together with an estimate of the property of the medium and a geometrical relationship between the first and second transmission paths to calculate a revised estimate of said property of the medium.

All of the preferred features described above in relation to the methods apply equally to the apparatus as will be readily apparent to a skilled person.

Viewed from another aspect, the invention provides a method of measuring the speed of sound of a medium using ultrasound, comprising: transmitting one or more ultrasound pulses into the medium from one or more transmitters and receiving at least a first echo signal and a second echo signal from within the medium at one or more receivers, wherein the first and second echo signals have travelled along first and second paths within the medium from the one or more sources to the one or more receivers, the second path being different from the first path; and using the difference in travel times along each of the first and second paths and the distances between source and receiver for each of the first and second paths to calculate the speed of sound in the medium.

It will be appreciated that using the difference in travel times may comprise using parameters derived from the difference in travel times, for example transformation into the frequency domain may change differences in travel times into phase differences in the frequency domain.

The calculation may also uses an estimate of the speed of sound and the calculated speed of sound may be an improved estimate of the speed of sound. The method may comprise performing the calculating step a plurality of times, each iteration using the improved estimate from the preceding step.

Viewed from another aspect, the invention provides a method of measuring properties of a medium using ultrasound, comprising: transmitting one or more ultrasound pulses into the medium from one or more transmitters and receiving at least a first echo and a second echo from within the medium at one or more receivers, wherein the first and second echoes have travelled along first and second paths within the medium from the one or more sources to the one or more receivers, the second path being different from the first path; and using the angle between the two transmit directions and velocities measured along the two paths to calculate the flow or particle movement direction and/or magnitude within the medium.

The calculation may also use an estimate of the flow or particle movement direction and/or magnitude within the medium and the calculated flow or particle movement direction and/or magnitude may be an improved estimate of the flow or particle movement direction and/or magnitude within the medium. The method may comprise performing the calculating step a plurality of times, each iteration using the improved estimate from the preceding step.

Viewed from another aspect, the invention provides a method of measuring properties of a medium using ultrasound, comprising: transmitting one or more ultrasound pulses into the medium from one or more transmitters and receiving echoe(s) at one or more receivers, wherein the receiving echoe(s) have travelled along at least two different paths in the medium from the one or more sources to the one or more receivers; and using the characteristics of the at least two recorded signals from any received echoe(s) together with any given estimate or given value of a property of the medium and a geometrical relationship between the one or more transmitters and receivers and/or the angle of direction of the transmitted beams to calculate a revised estimate of said property of the medium.

In at least some preferred embodiments, the present invention is concerned with a method for calculation of medium behaviour or response and calculation of acoustic and mechanical properties of a given medium/body/substance examined with an ultrasound transducer (or any set of transmitters and receivers), by examining the characteristics in any given attribute (travel time, amplitude, frequency) of the transmitted and received acoustic wave for at least two given sets of source-receiver locations and/or at least two different sets of angles of the transmitted beam or wave front and/or two different propagation paths for the acoustic waves, and using the said characteristics of a given attribute of the acoustic waves and information about spatial source-receiver locations and/or beam angles and/or wave propagation paths in calculating the properties and features of the investigated medium.

An objective of at least some preferred embodiments of the invention is to provide a method for quantification of physical (e.g. acoustic and mechanical) properties or characteristics of tissues by using conventional equipment for ultrasound examination, including conventional ultrasound transducers and associated apparatus, and the basic principles of pulse-echo imaging. This has numerous practical applications within medical ultrasound imaging, monitoring of treatment effects on biological tissue using acoustic waves/pulses, and also other measuring techniques involving transmission and receiving of acoustic waves, including industrial applications.

One object of at least some preferred embodiments of the invention is to quantify speed of sound in the body explored with ultrasound imaging, in order to provide a more accurate conversion of travel time to depth, and thereby producing ultrasound images with a more accurate localization of tissues in depth. This may be beneficial for guiding of interventional instruments, guiding of radiation therapy, guiding and monitoring of high-intensity focused ultrasound (HIFU), monitoring of treatment in general, as well as for diagnostic purposes.

The quantification of relative time delays for various source receiver distances, or any parameters derived therefrom, may also be used for correction of beam paths on the transmission of acoustic waves in order to form the smallest possible beam width at a given focus depth. Thus, the calculated time delays could be fed into the transmit circuit of the ultrasound probe, having different time delays (phase shifts) for the transmitted pulse for some group of elements. This may be used to improve resolution and thereby the image quality of the ultrasound images, but also for precise targeting of a region within the body for the therapeutic use of ultrasound.

Another objective of at least some preferred embodiments of the invention is to provide a method for real-time, almost real-time, or offline calculation of acoustic and mechanical properties of tissues, by monitoring changes in time delay, amplitude or shift in frequency versus beam angles or spatial source-receiver localization, or any parameters derived thereof.

The attenuation of the investigated medium could be estimated by considering the relative change in amplitude at any depth for at least two of any source-receiver locations or propagation paths.

Another objective of at least some preferred embodiments of the invention is to estimate the true velocity of flow in blood vessels. This solves the problem of the measured blood flow velocity being dependent on the angle between the ultrasound beam and the direction of flow. Based on the principles of the invention it is possible to calculate the angle between the ultrasound beam and the direction of flow, and thereby to calculate the true, or real, velocity of the flow. This has numerous clinical application areas, in which flow measurements are involved, both for blood flow and estimation of tissue movements.

Another objective of at least some preferred embodiments of the invention is to measure and estimate the response of the medium when exposed for any set of forces. The invention makes it possible to calculate the direction of the deformation (resulting from the net force acting on the medium) by considering changes in a given attribute obtained from examining a given region of interest (ROI) with at least two different acoustic waves having different paths of travel (due to different beam angles, or source-receiver localization). The method makes it possible to estimate the maximum displacement occurring in the medium, and to calculate the resultant displacement in any given direction. The method is therefore suitable for estimation of any parameter that can be derived from the displacement in the medium. The method is suitable for estimation of strain in the tissue, obtaining values for axial strain, lateral strain, elevation strain, shear strain, axial shear strain, lateral shear strain as well as strain rate measurements. The method is also suitable for estimation of Poisson's ratio, and other parameters describing the behaviour of the tissue when exposed for any kind of stress or forces.

Another objective of at least some preferred embodiments of the invention is to quantify anisotropy in a given medium using acoustic waves, by estimating changes in a given property in different directions. The method could be especially suitable for implementation in multi-row arrays or 2D arrays, as the relative change in attributes with source-receiver location and/or beam angles and/or beam paths could be explored in three-dimensional space or 4D (3D+ time).

The above methods may all also be used for industrial applications, such as inspection of constructions, estimation of thickness in e.g. corrosion analysis and estimation of material properties such as e.g. speed of sound of any medium.

Certain preferred embodiments of the invention will now be described, by way of example only, and with reference to the accompanying drawings in which:

FIGS. 1A-D show various examples of source/receiver locations on a transducer;

FIG. 2 illustrates plane wave transmission at different angles;

Figure 5:
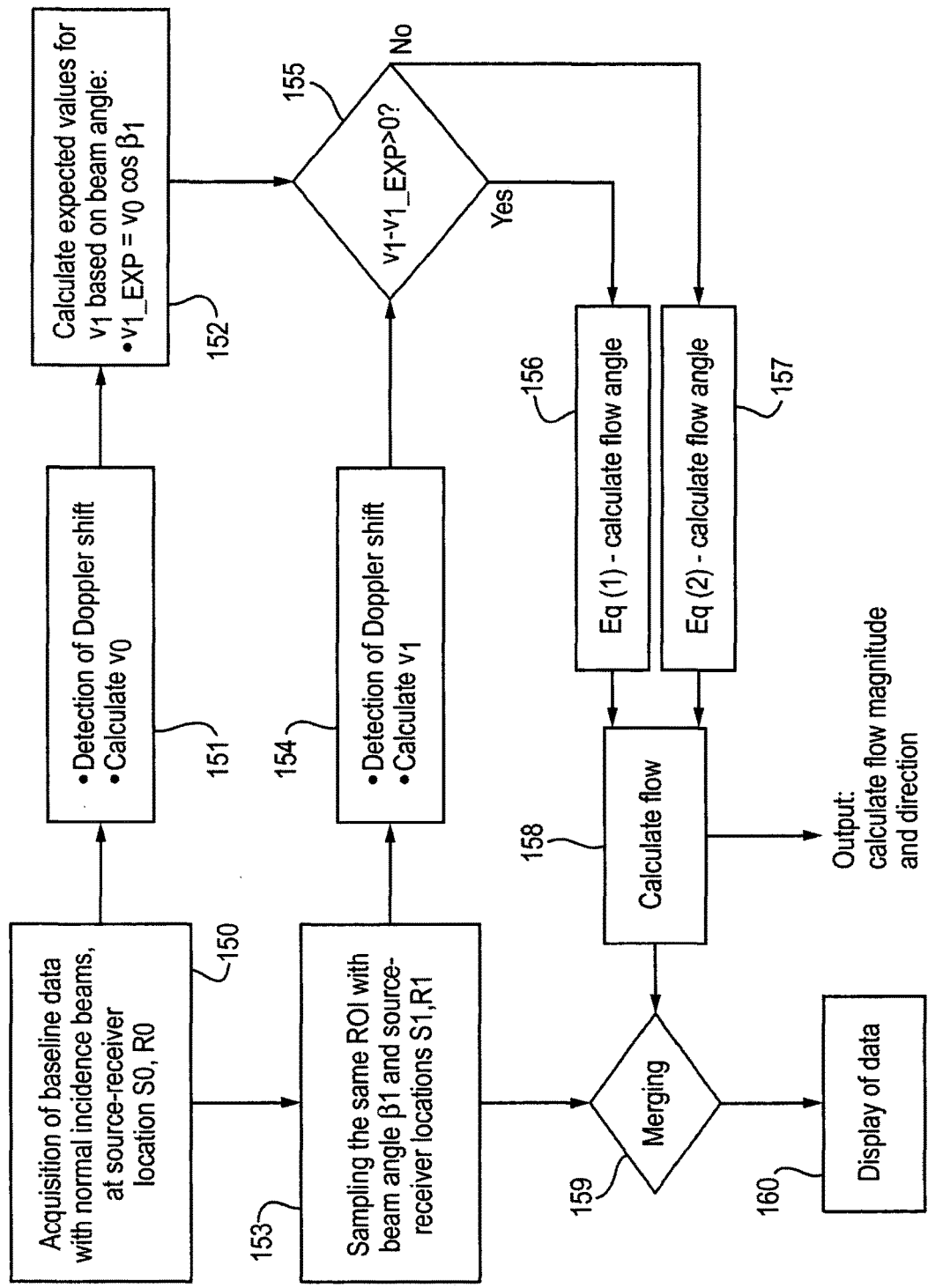
Figure 10A:
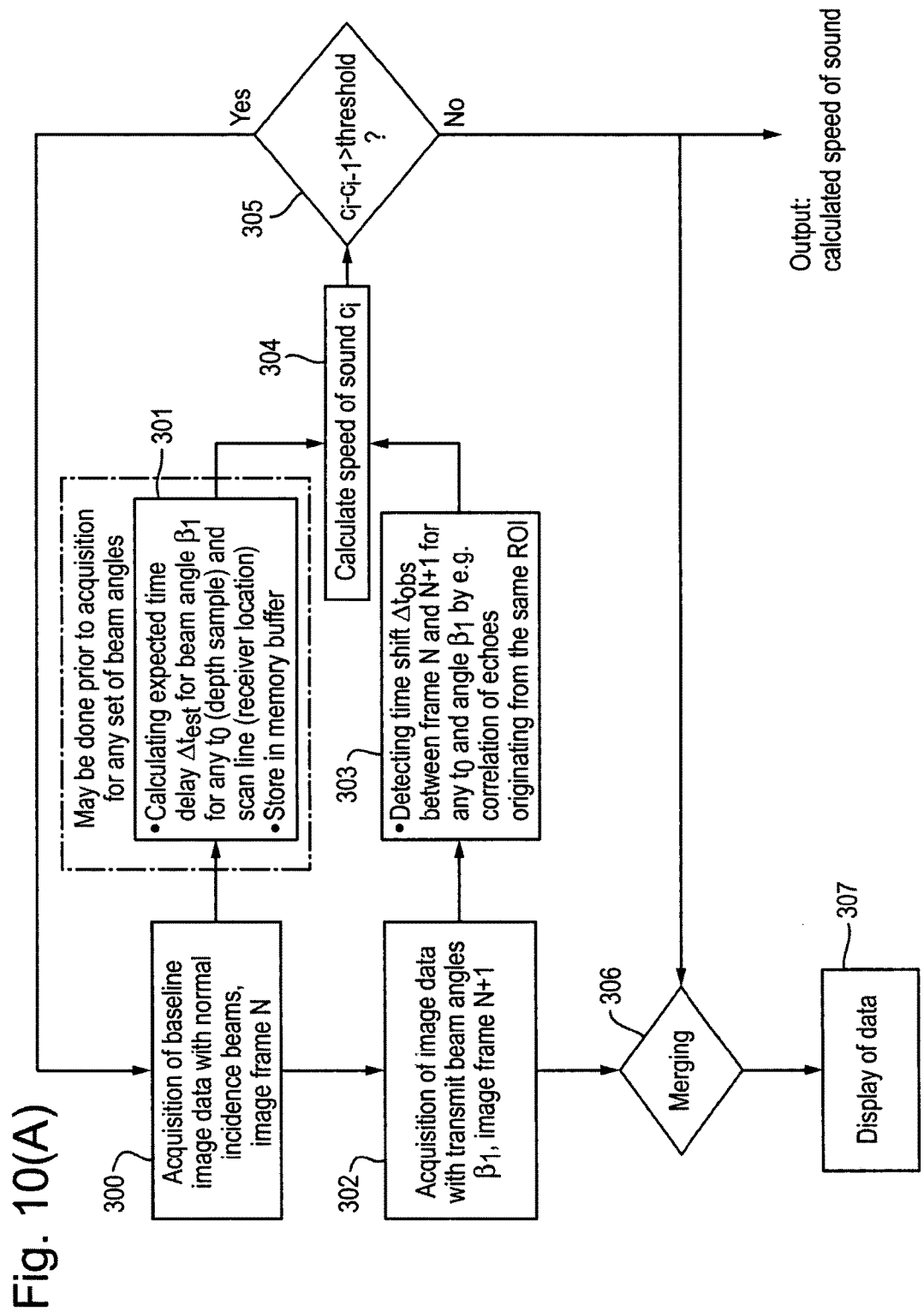
Figure 10B:
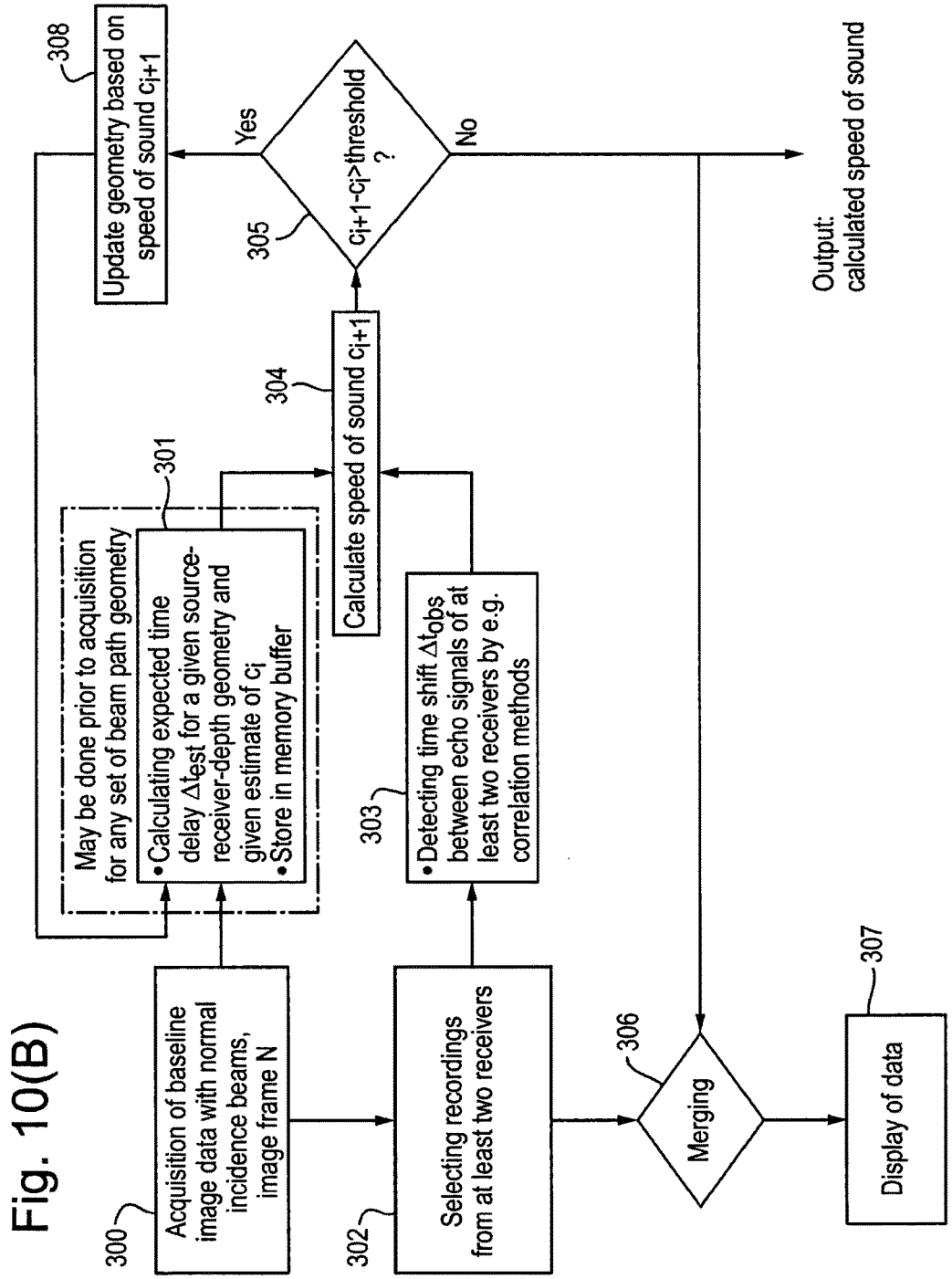
Figure 14:
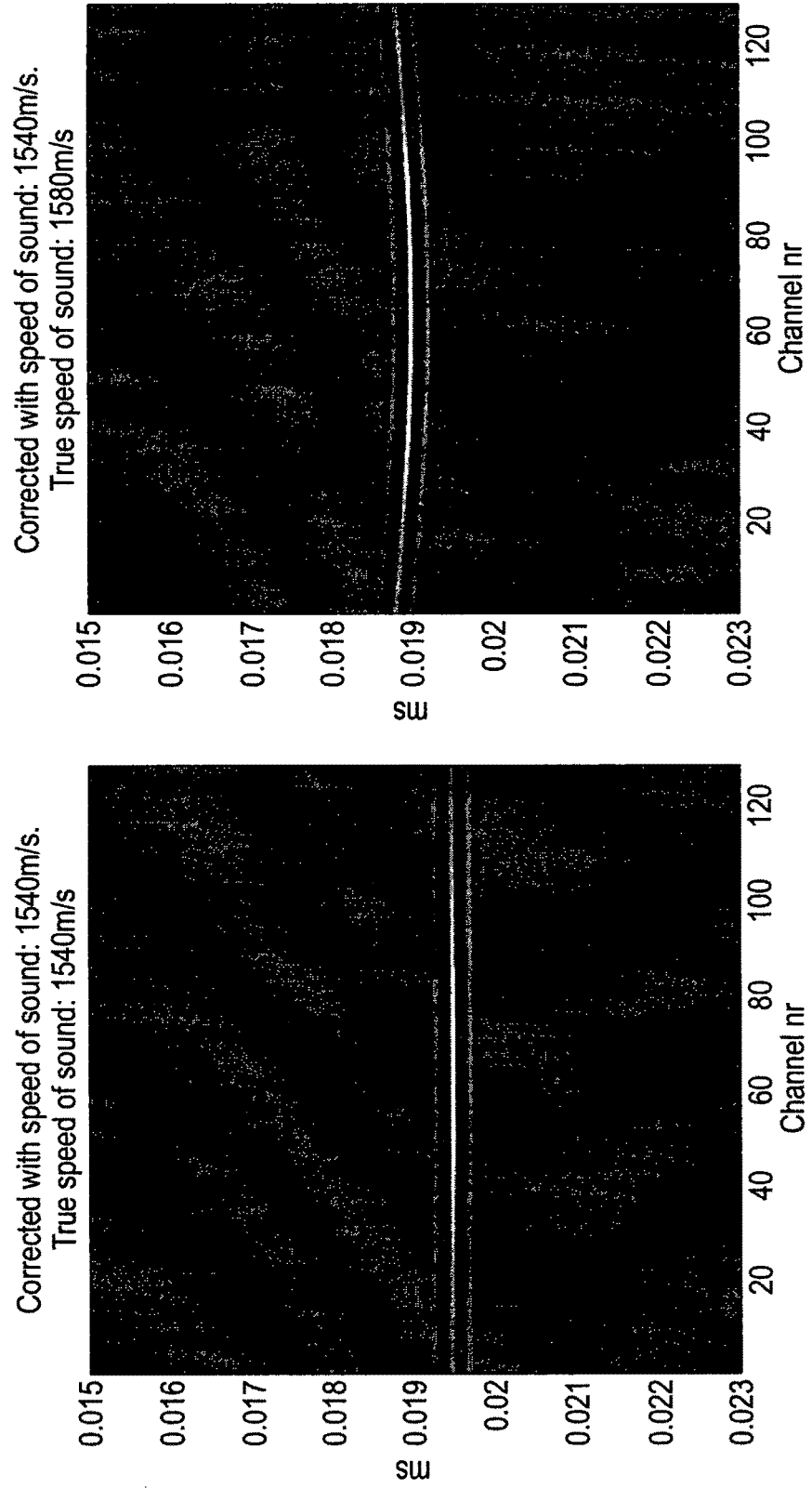
Figure 15:
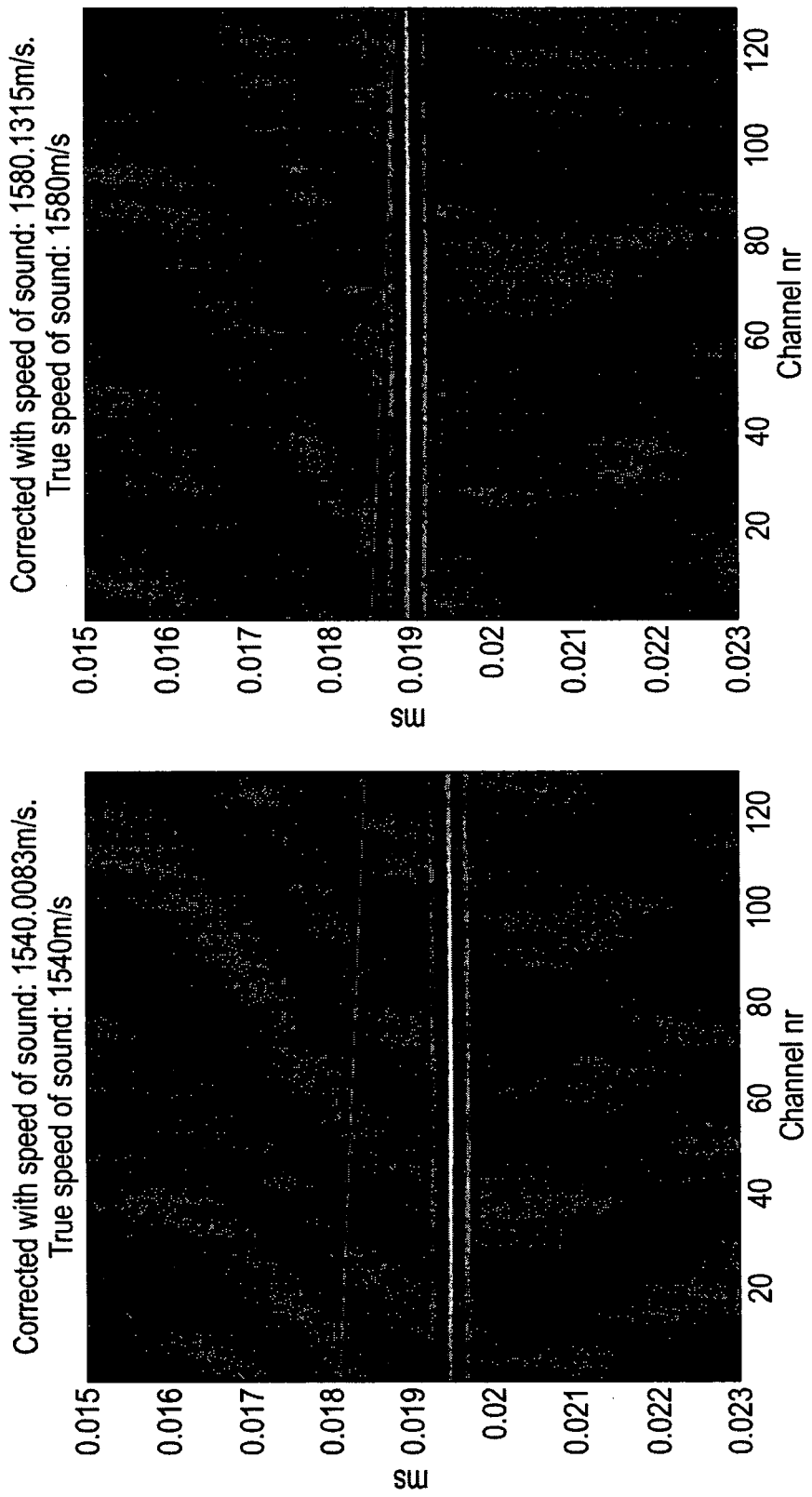
Figure 16:
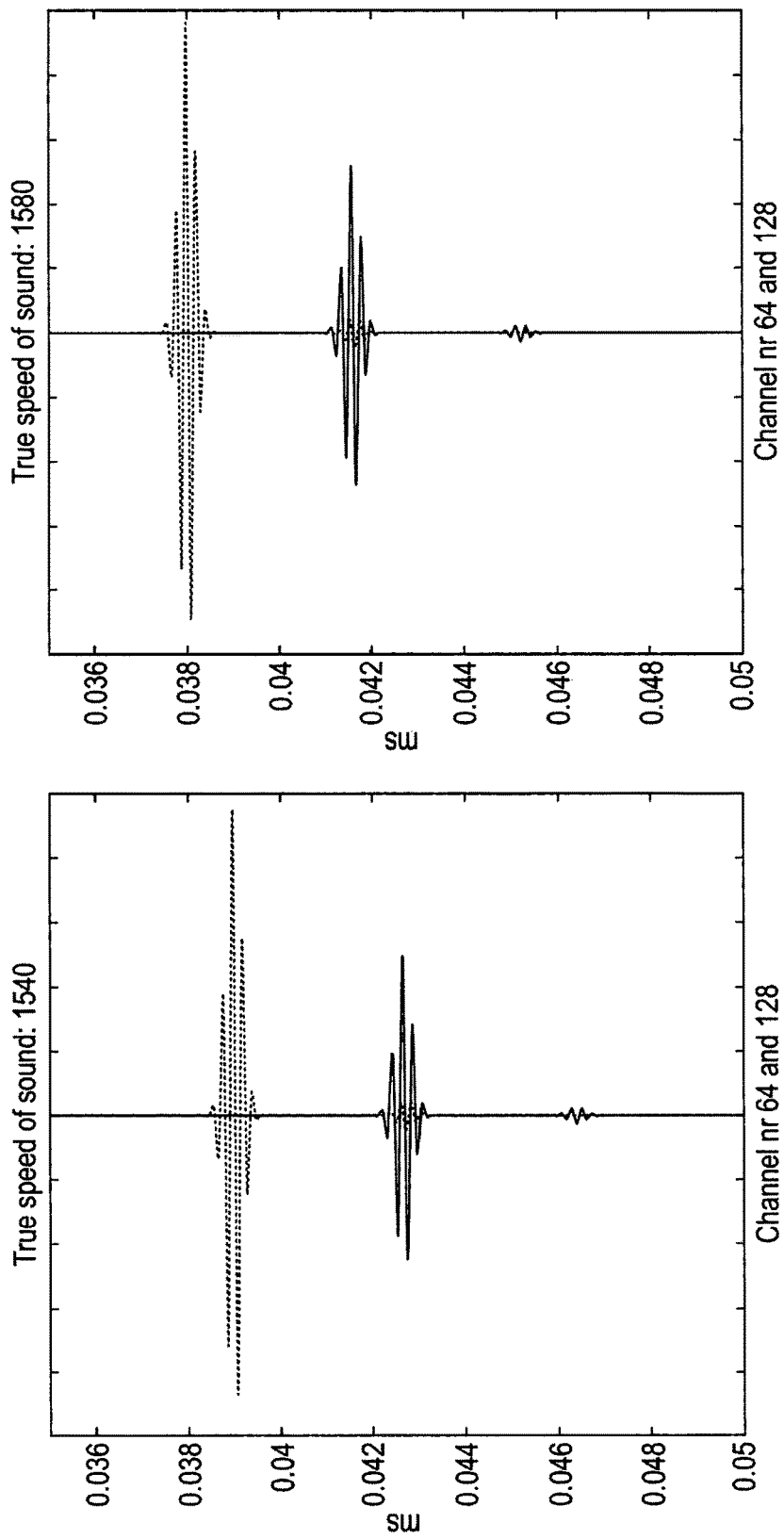

FIGS. 4A-E show different relationships between a transducer and a blood vessel and corresponding measurement vectors;

FIG. 5 is a flow diagram of an example process for flow angle measurement;

FIG. 6 illustrates flow measurement with more than two measurements;

FIG. 7 illustrates flow measurement using curve fitting with extrapolation and interpolation;

FIG. 8 is a flow diagram of an example process for analysis of displacements;

FIG. 9 illustrates measurements of the speed of sound within a medium;

FIG. 10a is a flow diagram of an example process for calculating speed of sound;

FIG. 10b is a flow diagram of another example process similar to FIG. 10a;

FIG. 11 illustrates multiple measurements of speed of sound at different locations within a medium;

FIG. 12 illustrates measurement of angle of inclination of an interface within a medium;

FIG. 13 illustrates the ultrasound response from a point scatterer in a medium at two different speeds of sound;

FIG. 14 illustrates the data of FIG. 13 corrected to remove the effect of geometrical differences due to the lateral offset of the receive elements;

FIG. 15 illustrates the data of FIGS. 13 and 14 following an iterative procedure to find the correct speeds of sound for the medium; and FIG. 16 compares the received pulses from two laterally spaced apart transducer elements in the various scenarios illustrated in FIGS. 13-15.

The methods for estimation of medium characteristics according to certain embodiments of the invention, explore the differences in a given attribute of the acoustic wave, for at least two different sets of source-receiver locations or at least two different sets of beam angles or beam paths, as illustrated in FIGS. 1A-D. Using the changes in the attribute and the spatial information about the source-receiver locations or beam angle, it is possible to calculate a broad range of parameters to characterize medium behaviour or properties.

FIGS. 1A-1D illustrate a number of examples of transmission paths that can be used in embodiments of the invention. In each case all beams are sent and received by a single ultrasound transducer module 100 that comprises an array of transducer elements 110 on its sensing face. The array of transducers may be a one dimensional array (a linear array) or it may be a multi-row array (i.e. a few parallel one dimensional arrays (sometimes referred to as a 1.5 dimensional array) or it could be a full two dimensional matrix array. In FIGS. 1A-1D, all beams are sent and received from a single transducer module. However, two or more transducer modules could equally well be used.

Figure 1A:
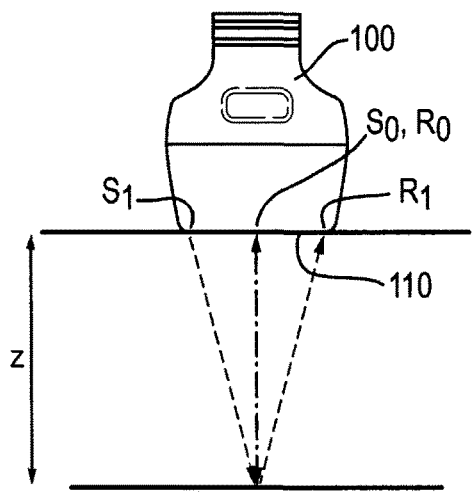
Figure 1B:
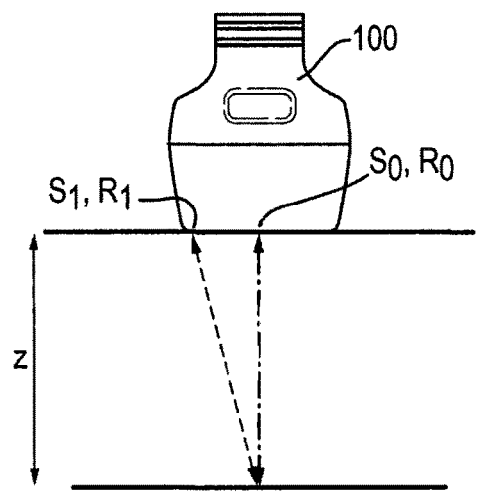
Figure 1C:
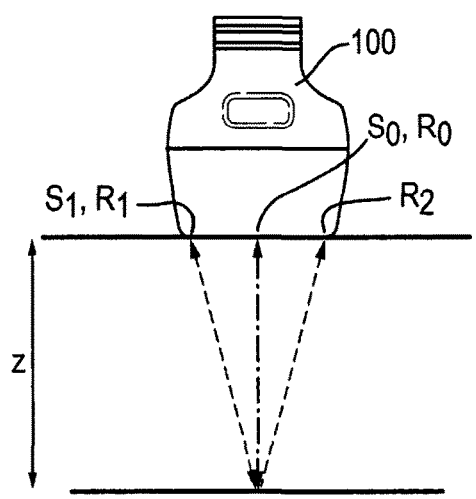
Figure 1D:
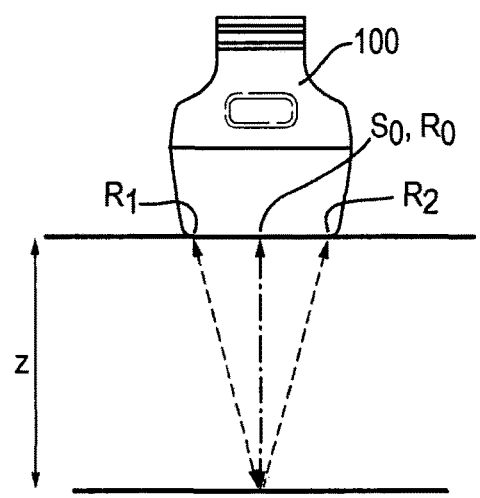

In FIG. 1A) an ultrasound pulse is emitted from the source S0, and the echoes originating from a given depth Z are reflected back to the receiver R0. Note that in FIGS. 1A-1D the source S0 is coincident with the receiver R0. Another acoustic pulse being emitted from source elements S1 is angled to sample the same point in depth, but the major part of the acoustic energy is received by elements R1. In FIG. 1A R1 is disposed on the opposite side of the transducer from S1, symmetrically either side of S0, R0 although they need not be symmetrical. Other examples are provided in FIGS. 1B, 1C and 1D. In FIG. 1B, the second receiver R1 is coincident with the second source S1. FIG. 1C is similar to 1B, but additionally a third receiver R2 is located opposite R1 and may receive echoes from pulses sent by either of sources S0 or S1. FIG. 1D has a single source S0 and three receivers R0, R1 and R2 all receiving echoes from S0 via different paths within the medium. In each case, the relative positions (and thus distances between sources and receivers) is known. The sources and receivers may be combined together into source-receiver pairs.

Different source-receiver pairs define different transmission paths through the medium.

The method may be implemented with any combination of number of sources and receivers, for example one emitted pulse could be received by several receivers (e.g. FIG. 1D). The term source and receiver is in this context used for a given location where an acoustic wave or pulse is radiated by any means or technology, and a given location where the acoustic wave or pulse is received or recorded by any means or technology. Typically, in ultrasound the source elements may also be able to receive and record data, and vice versa. The source and receivers may consist of several elements and not only a single unit. Transducer elements may be switched between transmit and receive modes. The source and receiver may have any shape and size, and may be 1-dimensional, multi-row or 2D. In ultrasound imaging the method is adaptable to any array design, as e.g. linear arrays, curved-linear arrays and phased arrays. The method of the invention may be applied on 1D, 2D, 3D or 4D data. The methods of the invention can be implemented at any appropriate stage in the acquisition and processing of the acoustic data. Further the methods of the invention may be implemented in any suitable domain for calculation, including time domain, frequency domain, f-k domain, etc.

In FIG. 1A-D the beams are only shown as lines for illustration. This is a schematic representation and does not provide a true representation of the wave propagation or the wave front. The methods of the invention can be used for any type of beam forming, including focused beams and plane wave methods, as well as in combination with external forces applied in one or several spatial locations (acoustic force, mechanical force) or internal forces acting on the said medium.

The methods could be implemented in an ultrasound system using conventional beam forming, in which a narrow beam is having a focus zone at a given depth. The method is also well suited for implementation in plane wave approaches, in which plane waves are transmitted from the array. The invention could be implemented by sending at least two plane waves with different angles into the medium to investigate. This is illustrated in FIG. 2 in which FIG. 2A shows a plane wave perpendicular to the transducer surface 105 and FIG. 2B shows a plane wave at an angle to the transducer surface 105. The transducer shown in FIG. 2 has an array of N elements 110. In FIG. 2A there is zero time delay between the pulses sent from each of the N elements. In FIG. 2B there is a time lag between the transmission of the pulses from the N elements creating a wave front propagating with an angle relative to the surface of the transducer array 110. For the echoes originating from a given ROI the characteristics of any given attribute obtained with the two wave fronts with different angles relative to the transducer surface could be recorded and used for estimation of media characteristics and parameters.

The following examples relate to estimation of true velocity of flow or of any moving parts within a medium explored by Doppler mode.

As demonstrated below, it is possible to quantify the true blood flow velocity, independent of the angle between the transducer, or any source or receiver, and the blood vessel. It is also possible to measure the true velocity of any compartments or particle within a medium, when the medium or parts of the medium is exposed to any sort of stress or forces. The basic principles for both approaches are the same and rely on exposing a given region of interest (ROI) within the medium with acoustic waves along at least two different beam paths caused by a difference in transmit angles and/or source-receiver locations, and then use the frequency modulation (Doppler shift) or any parameters derived from the Doppler shifts for the at least two different wave propagation paths (beam paths), or directions of measurements, for subsequent calculation of angle or direction of the movement or flow relative to a reference angle that could e.g. be defined by a plane perpendicular to the transducer surface. The same method may be applied to any other parameters that may be derived from the observed Doppler frequency shift of the at least two acoustic waves. Thus, any given ROI (spatial position and depth) or sample in a dataset is associated with at least two different velocity (or Doppler shift) measurements, each associated with a given transmit magnitude and beam angle or source-receiver localization. By using geometrical calculations or other appropriate and known principles of calculations, the angle of orientation/direction of flow or particle movement compared to the transducer surface can be determined, and hence it is possible to calculate the true blood flow or particle velocity. The results of the angle determination or velocity measurements can be output to a file, display or image. The results of the method can also be used for subsequent analysis of data, and thereby improve the accuracy of established methods such as e.g. strain-rate-imaging, strain imaging, tissue Doppler imaging, and any other methods based on analysis of velocity or displacement of tissue, particles or liquids, in any given dimensional direction and with time.

The method of the invention may be realized in several different ways. The following examples show some possible implementations of the method. Other alternative implementations can also be derived by a person of ordinary skill in the field of the invention.

According to some preferred embodiments, the basic principle for detecting the angle/direction of flow or particle motion or displacement and the velocity or magnitude of flow/motion/displacement/deformation or the measurement of direction and/or magnitude of any particle movement in the medium at any region of interest, can be described as follows for the case of using two different measurement directions separated with an angle $\beta$ to measure the angle and velocity of flow:

1. The velocity of flow is measured in a given first direction;
2. A reference velocity value is calculated from the first velocity multiplied by e.g. the cosine of the angle $\beta$ between the measurement directions;
3. The velocity of flow is measured in another direction, with angle $\beta$ to the first measurement direction;
4. If the velocity found in step 3 is different than the reference value found in step 2, the angle of flow is calculated by considering the angle formed by a resultant vector between the measurements with magnitude and direction given from step 1 and step 3;
5. The magnitude of velocity in the direction of flow is estimated from using previous measurements and the found angle of flow.

IMPLEMENTATION EXAMPLE 1

Figure 3A:
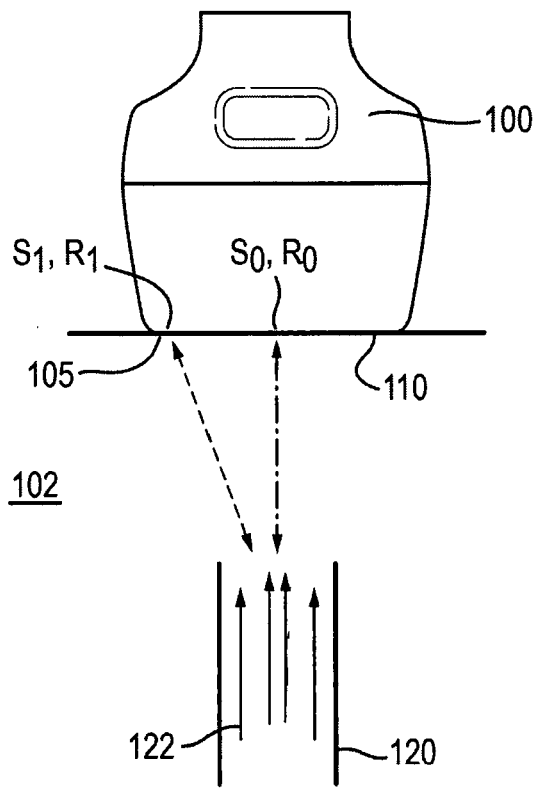
FIG. 3A illustrates measurement of a blood vessel.
Figure 3B:
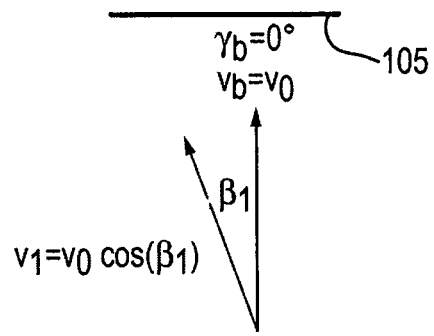
FIG. 3B shows vectors associated with the measurements in FIG. 3A.

One embodiment of velocity measurements is outlined in FIG. 3 (for illustration only, e.g. the lengths and angles of the vectors are schematically shown and are not necessarily to scale). FIG. 3A shows a conventional ultrasound transducer probe 100 investigating the velocity of flow in a blood vessel 120 oriented perpendicular to the plane of the transducer surface, using Doppler mode on the ultrasound scanner (not shown). The flow velocity is investigated with two consecutive acoustic measurements, one from the centre of the transducer array 110, (source S0 and receiver R0) and one from the edge of the transducer array 110 (source S1 and receiver R1). In each of these measurements the velocity is calculated from the received frequency modulation due to the Doppler effect. In FIG. 3B the measured velocity in each case is shown as a vector.

In FIG. 3B, $v_b$ is the blood velocity vector with an angle $\gamma_b$ relative to a plane perpendicular to the transducer surface, $v_0$ is the velocity vector measured at normal incidence, and $v_1$ is the velocity vector measured at an angle $\beta_1$ relative to a plane perpendicular to the transducer surface.

It will be appreciated that the flow in a blood vessel is merely one example of a situation in which this measurement technique can be used. The velocities of any other moving fluid flows or moving particles (e.g. cells or tissues) can also be measured. The tissue or medium may in addition be exposed to any kind of force to create a displacement or movement or deformation of the tissue, which can be detected and measured using this technique.

As shown in FIG. 3A a blood vessel 120 is situated perpendicular to the transducer surface 105, with blood flowing towards the surface (as indicated by arrows 122). The transducer probe 100 is used to examine the flow velocity using Doppler mode for two different transmit and receive angles of the ultrasound waves. In this "ideal case" (i.e. with the probe 100 aligned with the transducer array 110 perpendicular to the vessel 120) shown in FIG. 3A the beam sent from Source S0 and received by Receiver R0 is used to calculate the blood flow velocity by estimates from the Doppler shift. This is followed by examining the same region of interest (ROI) with an acoustic pulse emitted and received by S1, R1. As indicated in FIG. 3B, the estimated velocity $v_0$ for the normal incidence wave is in this ideal scenario (with the blood vessel oriented in a plane perpendicular to the probe surface, i.e. angle=0°) equal to the true blood flow velocity $v_b$. In this case the velocity $v_1$ measured in the same ROI with an acoustic beam transmitted with an angle $\beta_1$ relative to a plane perpendicular to the transducer surface is expected to be equal to $v_1 = v_0 \cos \beta_1$. Any deviation from this expected value can be assumed to be a result of a deviation from the ideal scenario, i.e. an angle other than 0° between the blood vessel and a plane perpendicular to the transducer surface.

The direction of the flow can be calculated by using at least two measurements of velocity or Doppler shift obtained for at least two different acoustic waves that cause echoes originating from the same ROI from different source/receiver locations.

FIGS. 4A-E illustrate the velocity vectors of two different acoustic beams examining the same ROI for five different scenarios of flow direction relative to a plane perpendicular to the transducer surface, represented by the angle $\gamma_b$. The figures shows that the angles $\alpha_1$ and $\eta_1$ between the resultant vector $a_1$ and velocity vectors $v_0$ and $V_1$, respectively, will change with the angle of the blood vessel. The angle of the blood vessel with respect to a plane perpendicular to the transducer array can be estimated by considering the change in angles $\alpha_1$ and $\eta_1$ that is defined by the velocities $v_0$ and $v_1$, which are obtained, or measured, by two different beam paths examining the given ROI in the medium.

By using e.g. geometrical considerations it can be derived that the angle of flow $\gamma_b$ can be determined from one of the equations:

$$\gamma_b = 90° - \sin^{-1}\left(\frac{v_0}{a_1}\sin\beta_1\right) \qquad (1)$$

$$\gamma_b = \sin^{-1}\left(\frac{v_0}{a_1}\sin\beta_1\right) - 90° \qquad (2)$$

where $a_1$ is determined by $a_1 = \sqrt{(v_0^2 + v_1^2 - 2v_0 v_1 \cos\beta_1)}$. The choice of which of equations (1) and (2) to use in the calculations may be based on the difference between the expected velocity $v_{1\_EXP}$ calculated from $v_{1\_EXP} = v_0 \cos \beta_1$ and the measured value for $v_1$. If $v_1 - v_{1\_EXP} \geq 0$ use equation (1), while if $v_1 - v_{1\_EXP} < 0$ use eq. (2).

Note that the angle of movement, particle motion or flow in this context means the angle of flow/motion relative to a plane normal to the transducer face. Flow or movement direction towards the transducer is an angle of 0 degrees and angles are measured anticlockwise from that reference. For the purposes of evaluating equations (1) and (2) above, velocity measurements are positive towards the transducer face and negative away from the transducer face.

The angle of flow is thereby calculated from the values of the Doppler shift, or velocities estimated therefrom, for the two acoustic beams targeting the same spatial ROI but having different propagation paths. In addition to the measured velocities the difference in angle between the two transmitted beams is used in the calculations.

It should be noted that more than one pulse is usually needed to perform Doppler measurements, which for the sake of simplicity is not elaborated here, but is well known to a skilled person.

It should be noted that alternative equations for calculating the angle of flow may be derived which are mathematically equivalent to the above, and which may be more computationally effective in terms of the processing power required to execute them. Also, other equations may provide more robust results.

Figure 4A:
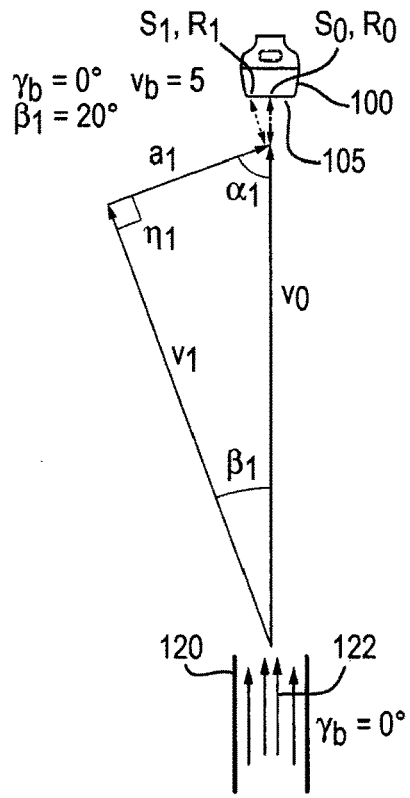

FIG. 4A shows a situation in which the flow 122 in the vessel 120 is towards the transducer probe 100 and perpendicular to the transducer face 105. The velocity $v_0$ measured perpendicular to the transducer face 105 is therefore equal to the actual (or true) flow velocity $v_b$. The velocity $v_1$ measured at an angle ($\beta_1$) of 20 degrees from the normal to the transducer face 105 is equal to $v_0 \cos(\beta_1)$.

Figure 4B:
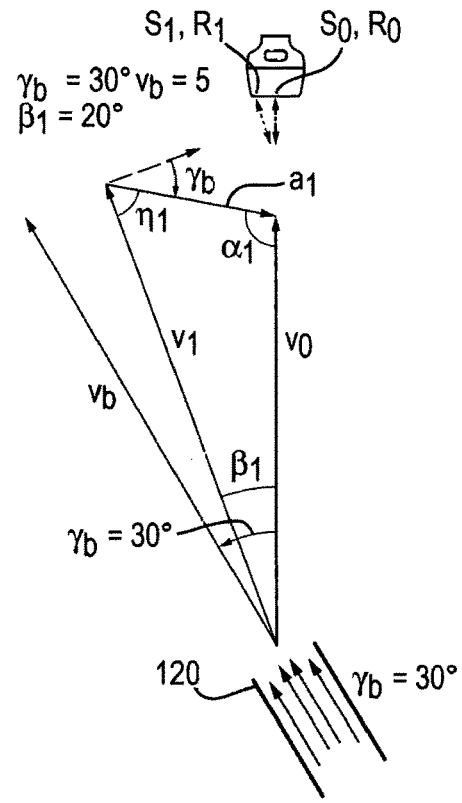

FIG. 4B shows the situation in which the flow 122 in the vessel 120 is towards the transducer face 105, but at an angle of 30 degrees to the normal ($v_0$ direction) and 10 degrees to the $v_1$ direction. The measured velocity $v_1$ is therefore greater than the measured velocity $v_0$.

Figure 4C:
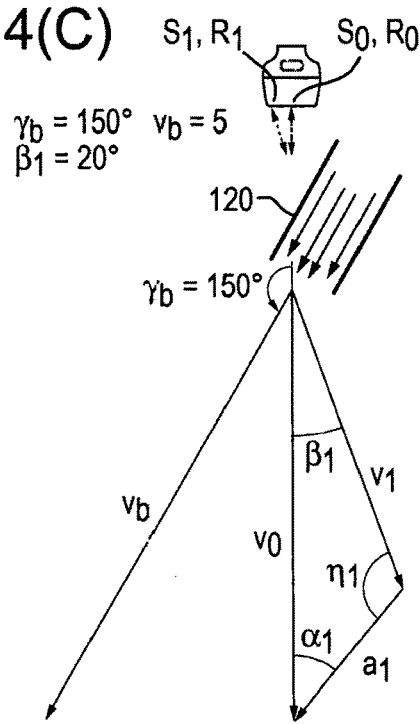

FIG. 4C shows the situation where the flow 122 is away from the transducer face 105 and is at an angle of 30 degrees to the normal. In other words, the angle between the true flow velocity and the vector normal to the transducer face 105 and pointing towards the transducer face 105 (the transducer-facing-normal) is 150 degrees. The angles from the normal vector facing the transducer to $v_0$ and $v_1$ are 180 degrees and 200 degrees respectively. As $v_1$ is the opposite side of $v_0$ from the true velocity vector, $v_1$ is less than $v_0 \cos(\beta_1)$ in magnitude. Both of the velocities $v_0$ and $v_1$ measured with Doppler mode will be negative (flow directed away from the transducer). The equation $v_1-v_{1\_EXP}$ will be larger than zero and so equation (1) applies rather than equation (2).

FIG. 4D shows a situation similar to FIG. 4C, but with the flow 122 in the vessel 120 at 210 degrees to the transducer-facing-normal so that $v_1$ lies between the $v_0$ direction and the true velocity direction $v_b$. Using Doppler techniques we find that the velocitiy $v_1$ is negative and greater in magnitude than $v_0 \cos(\beta_1)$. Equation (2) applies as $v_1-v_{1\_EXP}$ is less than zero.

In FIG. 4E the flow 122 in the vessel 120 again flows towards the transducer face 105 at an angle of 30 degrees to the normal as in FIG. 4B, but this time the flow 122 is in the opposite lateral direction, i.e. the angle to the transducer-facing normal is 330 degrees (or −30 degrees) and the normal measurement vector $v_0$ lies between the true velocity vector $v_b$ and the angled measurement vector $v_1$. $v_1$ is smaller than $v_0 \cos(\beta_1)$ so equation (2) applies.

The magnitude of the velocity of the flow or particle movement may be calculated from either of the measured velocities $v_0$ or $v_1$, for example using the equation:

$$v_b = v_0/\cos\gamma_b \quad (3)$$

One of several possible practical implementation of the invention is outlined in FIG. 5. The process begins at step 150 in the upper left corner of FIG. 5 in which a normal incidence beam is transmitted into the medium and echoes are received at normal incidence. The source and receiver positions for this step are as illustrated at $S_0$, $R_0$ in the previous figures for example. At step 151, the received echoes are processed to analyse the frequency spectrum and calculate a Doppler shift that has occurred. This can be converted to a velocity measurement $v_0$ using standard processing techniques. Note that the Doppler processing will likely return a velocity spectrum rather than a single value, but an average or maximum velocity (or other statistic) may be calculated for further processing. In step 152 the measured velocity $v_0$ is used to calculate an expected value of velocity that would be measured by the angled beam $v_1$ if the $v_0$ measurement has coincided with the true flow direction. This value $v_{1\_EXP}=v_0 \cos(\beta_1)$ is passed on to step 155 for comparison.

In step 153, the same region of interest (ROI) is sampled with a second acoustic beam at a different beam angle, from a different source-receiver pair such as $S_1$, $R_1$ in FIGS. 3 and 4. In step 154 the Doppler shift and corresponding velocity $v_1$ are detected and calculated in the same way as in step 151 and is passed on to step 155 for comparison.

In step 155 the measured velocity $v_1$ is compared with the $v_{1\_EXP}$ value calculated from $v_0$. This comparison determined which of equations (1) and (2) should be applied for calculation of the flow angle. If $v_1-v_{1\_EXP} \geq 0$ processing proceeds to step 156 in which equation (1) is used to calculate the flow angle. Otherwise, if $v_1-v_{1\_EXP}<0$ processing proceeds to step 157 in which equation (2) is used to calculate the flow angle.

In step 158 the flow is calculated and the velocity (magnitude and direction) are output for further use. The data are also output to step 159 where they are combined with the original echo data which can also be used for other purposes such as standard B-mode imaging for example. The flow data can be overlaid on such B-mode images or can be displayed alongside it on a display such as a computer monitor in step 160.

IMPLEMENTATION EXAMPLE 2

Other embodiments of the invention may also be implemented using more than two acoustic beams to examine the given ROI in the medium. A schematic of beam patterns for this implementation is illustrated in FIG. 6.

Figure 6A:
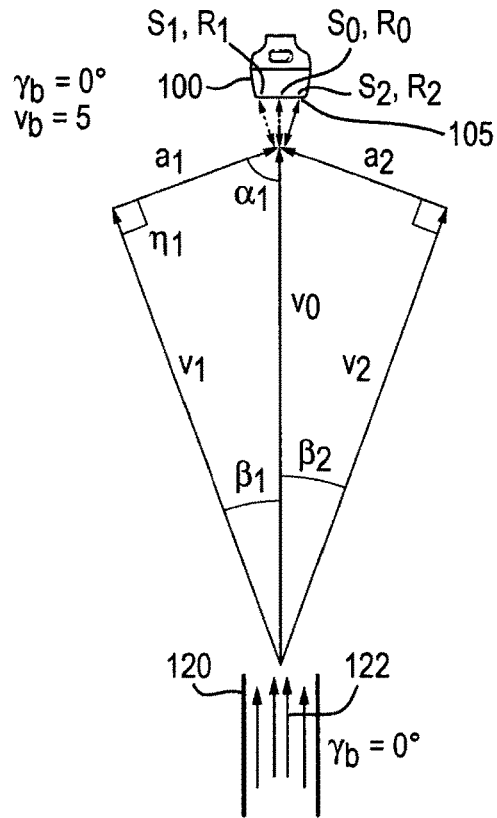
Figure 6B:
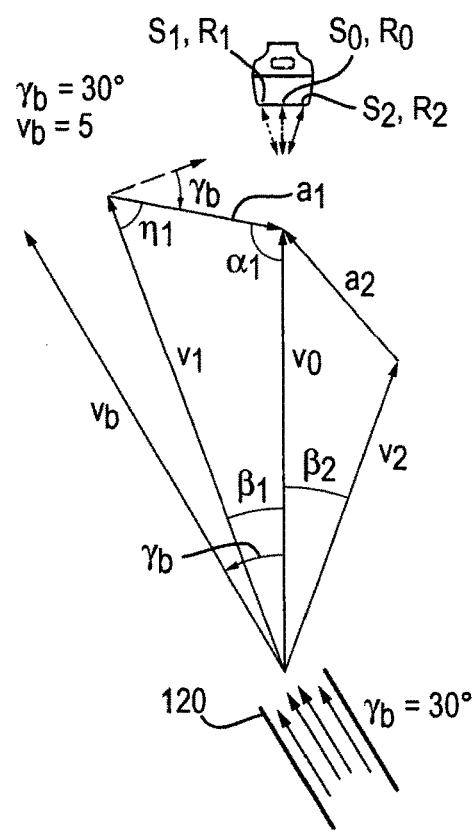

FIG. 6 is similar to FIGS. 3 and 4, but in addition to the measurements $v_0$ and $v_1$ (respectively from $S_0$, $R_0$ and $S_1$, $R_1$), a third measurement $v_2$ is taken from source $S_2$ and receiver $R_2$ located at the opposite end of the transducer array 110 from $S_1$, $R_1$ and generating a beam angled in the opposite direction to sample the same ROI as the other two beams. The angle between the beams for the $v_2$ measurement and for the $v_0$ measurement is $\beta_2$. FIG. 6A depicts motion directly towards the transducer ($\gamma_b=0$ degrees) and FIG. 6B depicts a vessel 120 with flow 122 oriented with an angle ($\gamma_b=30$ degrees) relative to a plane perpendicular to the transducer surface 105. In the arrangements shown here $\beta_1$ and $\beta_2$ are both 20 degrees, but they need not be the same angle.

The estimation of the angle of flow or particle motion can be derived by using two different equations exploring the difference in angle between the velocity vectors $v_0$, $v_1$, $v_2$ and the resultant vectors $a_1$ and $a_2$ in a similar way as shown in Implementation Example 1 above:

If $v_1-v_2>0$ then select Eq. 1 for calculating the angle of flow or particle motion, if $v_1-v_2<0$ then use Eq. 2. This may be computationally more efficient as a simple subtraction and comparison can be performed far more rapidly than the cosine calculation used in Implementation Example 1. The additional acquisition required for this example can be done simultaneously with the other acquisitions so as not to slow down the process.

In addition, the extra velocity measurement can be incorporated into the calculations if desired to improve the accuracy of the calculated values for the true flow angle and magnitude.

IMPLEMENTATION EXAMPLE 3

The velocity of flow or particle motion can also be found using a more exploratory use of acoustic beams, exploring the same ROI within the medium with acoustic waves with a multiple of beam paths. The magnitude of the flow velocity or particle movement can then be found by interpolating, extrapolating or curve fitting of the obtained velocity associated with the different acoustic waves, and thereby predicting the maximum magnitude of velocity and optionally the direction of flow at which the maximum occurs, based on the previously obtained measurements of velocity using different beam paths. The principle of interpolating, extrapolating or using curve-fitting methods to estimate the flow or particle velocity is schematically shown in FIG. 7.

Figure 7A:
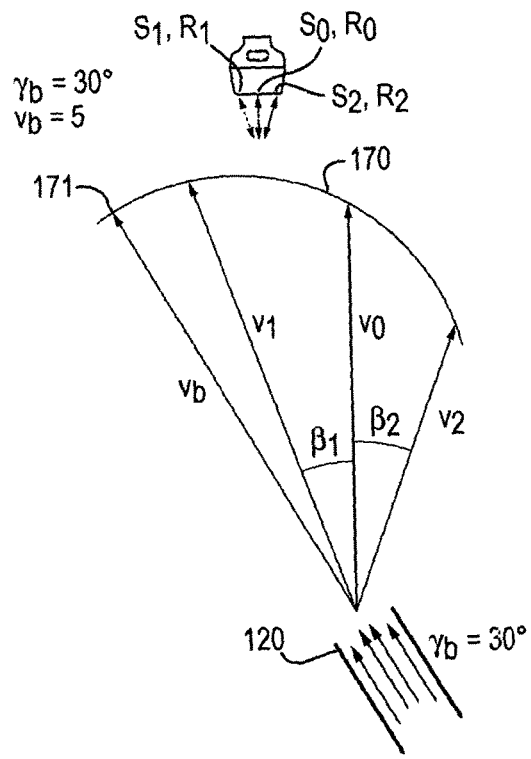
Figure 7B:
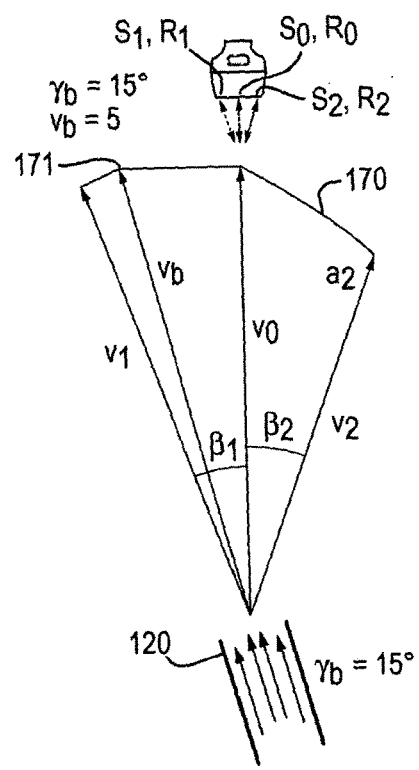

FIG. 7 shows measurements similar to those of FIG. 6, i.e. three measurements taken from three different source-receiver locations. FIGS. 7A and 7B are two different angles of the vessel 120. The line 170 in FIGS. 7A and 7B is a curve fitted to the measured vectors $v_0$, $v_1$ and $v_2$. In FIG. 7A the curve is extrapolated to find the point 171 at which a maximum magnitude vector occurs. This is determined to be the true velocity vb and the direction at which it occurs is the direction of flow 122 in the vessel 120. Similarly, in FIG. 7B the measurement data points which form curve 170 are interpolated to find the maximum 171 and the direction at which it occurs.

Thus, the calculated velocity of flow or particles within a given medium using the current approach is a result of exposing a given ROI within the medium with acoustic waves having different propagation paths, and using the attributes of the acoustic waves and information about the spatial location of source receiver locations or beam angles for estimation of parameters and characteristics of the investigated medium It should be noted that any sets of beam angles and/or source-receiver locations might be used in the implementation of the invention shown in all examples, and the beam paths are not limited to those shown in the figures. It should also be noted that the output of the method is not necessarily an image, but could also be displayed as numbers, written to a file or used as input in subsequent calculations.

The following illustrates how the above described methods can also be used for estimation of displacement, velocity, strain, strain rate or elastic properties in a medium by analysis of reflected or backscattered events.

Embodiments of the invention may also be applied on analysis of displacement, velocity, strain, strain rate and other parameters involving the study of media response to any set of forces. The force or stress acting on a medium or tissue may be generated internally from e.g. physiological and biological processes, or be applied externally by using e.g. radiation force or any other mechanical force such as palpation by a clinician. The method of the invention may be applied by following the same approach and principles as described in the previous section with reference to examples 1-3. However, the measurement of the displacement or other responses of the medium when exposed to a set of forces does not have to be based on Doppler shift methods as described in the previous examples. The method may be applied on any data being echoed or propagating from an interface back to a receiver, as for example in conventional ultrasound brightness mode (B-mode) imaging. For simplicity, we will in the subsequent description only refer to measurements of displacements u, investigated by using a transducer for ultrasound B-mode imaging of a soft tissue. However, the invention may also be applied for measurements of other parameters and for other measurement systems involving propagation of waves.

The investigation of a given ROI with given spatial coordinates and depth using elastic or acoustic waves with different propagation paths follows the basic principles explained in the previous section. However, the measurement ROI (which may be represented by one or more sampling points, pixels or voxels) is associated with a set of at least two displacement attributes or values with a given magnitude and beam angle or source-receiver localization, instead of velocity as in the previous section. FIG. 3, FIG. 4, FIG. 6 and FIG. 7 are still valid to illustrate how a given ROI is examined by ultrasound in order to obtain measurements of the direction of displacement u relative to a plane perpendicular to the transducer surface or any other relevant reference plane. However, the velocity $v_0, v_1, \ldots$ measured at given beam angles should be replaced by the displacements $u_0, u_1, \ldots$ occurring as a response to any set of forces acting on the medium.

The Eqs. 1 and 2 can accordingly be restated as:

$$\gamma_u = 90° - \sin^{-1}\left(\frac{u_0}{a_1}\sin\beta_1\right) \quad (3)$$

$$\gamma_u = \sin^{-1}\left(\frac{u_0}{a_1}\sin\beta_1\right) - 90° \quad (4)$$

where $\gamma_u$ is the angle of the direction of displacement relative to a plane perpendicular to the transducer surface, where 0° indicate an angle of the measured displacement being perpendicular to the probe surface. The resulting length of side a can be calculated as $a=\sqrt{(u_0^2+u_1^2-2\ u_0\ u_1\ \cos\beta_1)}$. The criteria for selecting the appropriate equation for calculation of the angle may be based on the difference between the expected displacement $u_{1\_EXP}$ calculated from $u_{1\_EXP}=u_0\cos\beta_1$ (i.e. on the provisional assumption that displacement is perpendicular to the transducer face) and the measured value for $u_1$. If $u_1-u_{1\_EXP}\geq 0$ use equation (4), while if $u_1-u_{1\_EXP}<0$ use eq. (5).

The magnitude of displacement in the estimated angle from Eq. 4 or 5 can be estimated from:

$$u_d=u_0/\cos\gamma_u \quad (6)$$

As for the case with determination of particle velocity using Doppler data, the magnitude of displacement occurring in the direction $\gamma_u$ can be estimated from the found angle of direction for the displacements or movement relative to the probe surface, which is calculated by measuring displacements occurring in at least two different propagation paths for the acoustic waves examining a defined ROI.

The implementation examples in the previous section may also be adapted and applied for the purpose of estimation of displacements in the medium. The most important practical difference is that the displacements along the axial direction of the ultrasound data need to be estimated, instead of the velocity found by Doppler mode ultrasound. The displacements at any depths can be found by e.g. acquiring at least two images for each beam angle, and finding the displacement along the beam (axial direction) by using any known methods for estimation of time delays, as e.g. the autocorrelation and 2D cross-correlation method. The correlation may also be done in the lateral direction, i.e. across beams, in order to estimate time delays between beams in the lateral directions. However, the estimation of time delays is more commonly performed in the axial direction. Based on the magnitude and angle of the displacements for a given ROI, the angle for the direction of the displacements (or particle motion) relative to the transducer surface (or any other suitable reference) may be calculated, as well as the magnitude of the displacements in this direction. A coarse overview of a possible practical implementation is shown in FIG. 8.

FIG. 8 is a flow diagram illustrating the measurement and calculation process similar to FIG. 5. The process begins at step 180 in the upper left corner of FIG. 8 in which a normal incidence beam is transmitted into the medium and echoes are received at normal incidence. The source and receiver positions for this step are as illustrated at $S_0$, $R_0$ in the previous figures for example. Data is acquired for two successive image frames, i.e. two successive pulses transmitted from $S_0$ with the corresponding receive signals for each pulse being received at $R_0$. At step 181, the received echoes for the two frames N and N+1 are compared and processed to determine time delays between the pulses. This may be done using correlation techniques for example. This can be converted to a displacement measurement $u_0$ using standard processing techniques. In step 182 the measured displacement $u_0$ is used to calculate an expected displacement value that would be measured by the angled beam $u_1$ if the $u_0$ measurement has coincided with the true displacement direction. This value $u_{1\_EXP}=u_0\cos(\beta_1)$ is passed on to step 185 for comparison.

In step 183, the same region of interest (ROI) is sampled with a second acoustic beam at a different beam angle, from a different source-receiver pair such as $S_1$, $R_1$ in FIGS. 3 and 4. Again two successive frames are sampled using successive pulses N+2 and N+3. In step 184 the displacement $u_1$ is detected and calculated in the same way as in step 181 and is passed on to step 185 for comparison.

In step 185 the measured displacement $u_1$ is compared with the $u_{1\_EXP}$ value calculated from $u_0$. This comparison determined which of equations (4) and (5) should be applied for calculation of the angle of flow or particle motion. If $u_1 - u_{1\_EXP} \geq 0$ processing proceeds to step 186 in which equation (4) is used to calculate the angle of displacement. Otherwise, if $u_1 - u_{1\_EXP} < 0$ processing proceeds to step 187 in which equation (5) is used to calculate the angle of displacement.

In step 188 the displacement magnitude and direction are output for further use. The data are also output to step 189 where they are combined with the original echo data which can also be used for other purposes such as standard B-mode imaging for example. The displacements or flow data can be overlaid on such B-mode images or can be displayed alongside it on a display such as a computer monitor in step 190.

Embodiments of the invention are well suited for analysis of deformation and motion, measured as a function of source-receiver location, beam angle (transmit and/or receive) or wave propagation path. The change in attributes can be used for calculation of material properties or the response of the medium. Based on the previous examples it should be well illustrated how the analyses may be performed and implemented, and a skilled person could translate the methods of the invention for use in quantitative assessment of elastic properties and parameters other than those mentioned here.

Embodiments of the invention can be used for estimation of the speed of sound using multiple source/receiver locations and/or beam paths in the medium to obtain an accurate measurement of the speed of sound.

The basic principle is that the speed of sound is calculated by exploring assets that are related to the travel time between acoustic pulses, or waves, having a different wave propagation path in the investigated medium. The medium could be any biological tissue, solids, gas or fluids. The different wave propagation paths of the acoustic pulses or waves can be introduced in the medium by using for example an ultrasound transducer array. The sound can be emitted and/or recorded using different source-receiver elements, or by using different beam angles. A given region of interest in the medium is therefore investigated with pulses having at least two different propagation path lengths. As the travel time is related to both speed and travel path length, the travel time for a medium with a given speed of sound will be different for pulses having different propagation paths.

The steps below can exemplify the method of the invention for estimation of wave propagation velocity in a given medium:

1. The travel time for a transmitted and echoed pulse or wave for at least two different wave propagation paths is recorded for a given region of interest in the investigated medium.
2. The difference in travel time for the two recorded signals is found
3. The observed difference in travel time is compared to a reference difference in travel time, the reference value may be estimated from the given source and receiver geometry and a given speed of sound, or be calculated from a previous estimate of the speed of sound.
4. Any deviation between the observed difference in travel time and the reference difference in travel time can be assumed to be related to a different speed of sound in the investigated medium, compared to the speed of sound setting used initially (e.g. the speed of sound c set in the ultrasound scanner) for the estimated reference value.
5. The speed of sound of the investigated medium can be expressed by relating the observed travel time difference for an echo originating from a given depth to the reference difference in travel time as expected or anticipated by e.g. geometrical considerations of travel length based on the source and receiver elements locations and/or angular measures related to the ultrasound beam angle.
6. The method may be implemented using an iterative approach, repeating the estimates of speed of sound until the observed difference in travel time and the estimated reference difference in travel time is similar by a given order of accuracy.

The difference in travel time between the at least two signals may be calculated by for example correlation based methods, or by subtracting the travel time between similar features of the signals as e.g. the time between the maximum amplitude of the signals, or by other methods suitable for the purpose. The analysis of speed of sound may be repeated for any region of interests. The influence of curvature or angle of a given imaged object may be compensated for, as shown later.

One implementation of the principles of the invention is to calculate the change in travel time for a reflection occurring at a given depth d for at least two acoustic pulses with different wave propagation paths caused by differences in source-receiver location and/or beam forming (angles), as schematically outlined in FIG. 9.

Figure 9A:
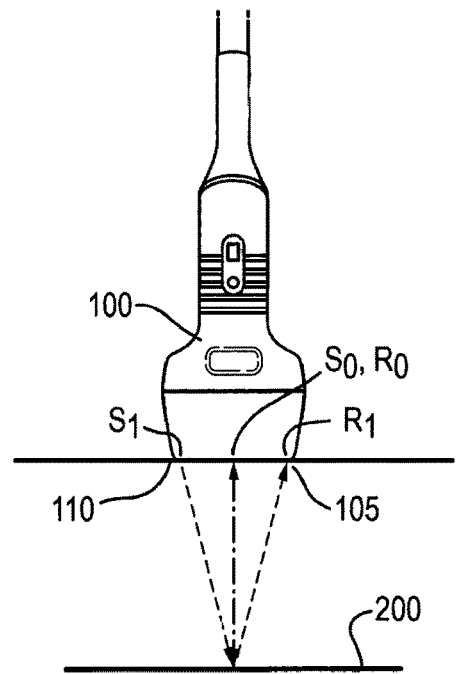

FIG. 9A shows the basic setup for speed of sound measurements. An ultrasound probe 100 with a transducer array 110 on its transducer surface 105 sends signals into the investigated medium along two or more different transmission paths to an ROI at depth d. For example, one signal may be sent from source $S_0$ and received at receiver $R_0$ (the direction normal to the transducer surface 105) and a second signal may be sent from source $S_1$ and received at receiver $R_1$ in the same way as described in the other embodiments above. The ultrasound transducers may be any kind of transducer technology such as PZT, CMUT, PMUT, etc. At also may be of any geometry, e.g. one dimensional, multi-row or two dimensional.

Figure 9B:
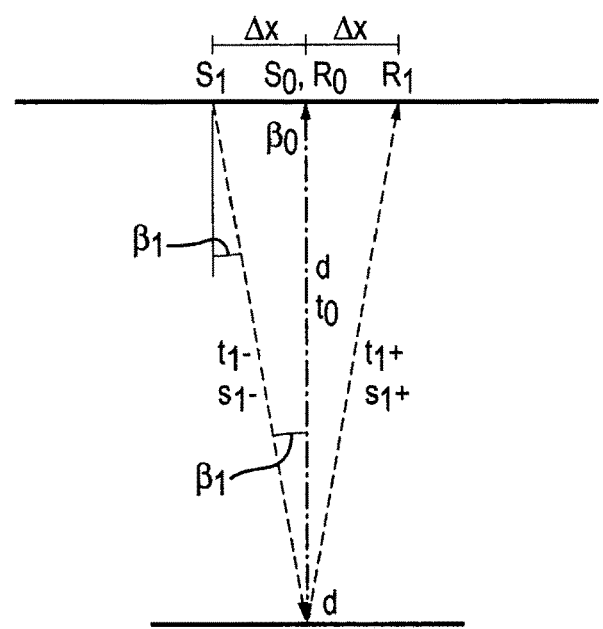

FIG. 9B shows the transmission paths schematically in more detail with the two way travel from source to depth point d and from d to receiver. Time $t_0$ represents the two way travel time from $S_0$ to depth d and back to $R_0$. The travel time from $S_1$ to depth d is $t_1/2$ which is also the travel time of the acoustic pulse from d to $R_1$. The lateral distance between $S_1$ and $R_1$ is $2 \Delta x$.

An acoustic pulse is transmitted from $S_0$, propagating at speed c to a depth d where an echo is formed at an interface 200 between two tissues and propagates back to the receiver location $R_0$. The simple equation for the total travel time $t_0$ for the transmission of the pulse and receiving the echo is given by:

$$t_0 = \frac{2d}{c} \qquad (7)$$

A second pulse is transmitted from $S_1$ (a distance $\Delta x$ from $S_0$, $R_0$), propagating to the same region of interest at depth d where an echo is generated and is propagating to the receiver $R_1$ (a distance $\Delta x$ the other side of $S_0$, $R_0$). The travel time $t_1$ for the propagation distance $s_1$. from source $S_1$ to the point of reflection at depth d is expressed by:

$$t_{1-} = \frac{s_{1-}}{c} = \frac{d/\cos\beta}{c} = \frac{t_0}{2\cos\beta} \tag{8}$$

Similarity.

$$t_{1+} = \frac{t_0}{2\cos\beta}$$

where $\beta$ is the angle of the transmitted beam relative to a plane perpendicular to the transducer surface. The total travel time for the acoustic pulse transmitted from $S_1$, reflected at depth d and received at $R_1$ can thereby be expressed as:

$$t_1 = t_{1-} + t_{1+} = 2\frac{t_0}{2\cos\beta} = \frac{t_0}{\cos\beta} \tag{9}$$

Thus, the travel time with the given source-receiver and depth can be related to the travel time for the normal incidence wave at the similar depth and region of interest. The difference in travel time $\Delta t$ related to the different paths of travel for the two different waves could accordingly be stated as:

$$\Delta t = t_1 - t_0 = \frac{t_0}{\cos\beta} - t_0 = t_0(1 - \cos\beta) = \frac{2d}{c}(1 - \cos\beta) = \frac{2\Delta s}{c} \tag{10}$$

where $\Delta s$ denotes the difference in travel distance between the propagated acoustic pulses. From this we observe that the difference in travel time can be calculated based on e.g. the travel time for normal incidence waves being reflected at a given depth, and the beam angles of the successive acoustic waves. The difference in travel time may alternatively be calculated by considering the depth of the target and the location of source and receiver elements.

The change in travel time for any pair of source-receiver locations may be theoretically calculated from equations stated above for wavelengths much less than the curvature of the reflecting interfaces in the medium. However, expressions for difference in travel time for waves propagating in a more complex medium are possible to derive. For example, the difference in travel time for two acoustic waves being reflected/scattered from a non-horizontal layer may be calculated. As shown in a later section methods according to embodiments of the invention may also be used for calculation of the curvature of an interface in the medium.

Based on the theoretical derived equations it is therefore possible to calculate the change in travel time for any set of source-receiver locations and for any depth. This may be calculated in advance and stored on the computer of e.g. an ultrasound scanner. The speed of sound for the investigated medium for the given spatial position of sources/receivers and given depth can be estimated by relating the measured time delay between e.g. a normal incidence wave and a wave transmitted with an oblique angle causing a reflection at the same point in depth with the theoretical derived estimate for time delay for a similar acquisition geometry and depth using a known value for speed of sound $c_0$. At a given depth the relation between estimated and measured difference in travel time for two acoustic waves with different beam angles can be stated as:

$$\Delta t = \frac{2\Delta s}{c_0} = \frac{2\Delta s}{c_0 + \Delta c} \tag{11}$$

Assuming that the spatial difference in propagation length $\Delta s$ should be identical for a given source-receiver arrangement and depth, any difference in the estimated and observed (or measured) time delay, $\Delta t_{est}$ and $\Delta t_{obs}$ must be addressed to a difference in speed of sound, $c_0 + \Delta c$. This can be stated as:

$$(c_0 + \Delta c)\Delta t_{obs} = c_0 \Delta t_{est} \tag{12}$$

and $$(c_0 + \Delta c) = c_0 \frac{\Delta t_{est}}{\Delta t_{obs}} \tag{13}$$

A higher observed/measured travel time delay than the theoretical obtained travel time delay would therefore imply a slower speed of sound in the explored medium, than the speed of sound used for the theoretical calculation of travel time delay. If one acoustic wave is transmitted along the normal incidence towards the probe surface (defined here as 0 degrees beam angle), the estimated difference in travel time for any beam angle can be expressed as a function of the travel time $t_0$ of the zero-degree beam (eq. 10) resulting in:

$$(c_0 + \Delta c) = c_0 \frac{t_0(1 - \cos\beta)}{\Delta t_{obs}} \tag{14}$$

It will be appreciated that other calculations could be made using any two beam angles, not necessarily including the normal incidence path to and from the transducer.

The theoretical calculations of change in travel time delay versus source-receiver location may be made more refined than expressed in Eq. 14. The calculations may e.g. include the effect of non-horizontal interfaces relative to the plane of the transducer surface in the medium explored. The curvature of the interfaces in a medium could be defined by the user, or estimated by a data driven method as shown in later sections of this document. The curvature of interfaces within the medium explored using acoustic waves may also be extracted manually or automatically based on the acquired images of the medium, and used for calculation of more exact travel time delay changes and thereby providing more accurate estimates of speed of sound.

The estimated time differences may also be established by experimental data from e.g. laboratory measurements. The expected time differences may also be derived from modelling of waves propagating in a given medium, using for example ray-tracing methods or finite element methods.

IMPLEMENTATION EXAMPLE 4

A schematic overview of a given implementation of the method for the purpose of estimation of speed of sound is shown in FIG. 10a. FIG. 10a is a schematic overview showing an example of a method for estimation of the speed of sound in a given medium when investigated using acoustic waves. The calculation of speed of sound for a given ROI may be done iteratively for improved accuracy of the calculated speed of sound.

The method begins in step 300 at the top left of FIG. 10a in which the first pulse is transmitted along the first beam path (at normal incidence in this embodiment). This pulse is denoted frame N and may be part of normal image data acquisition (e.g. B-mode imaging). Step 302 is similar to step 300, but relates to the second pulse transmitted at a different angle ($\beta_1$) along the second beam path.

Step 301 may be done prior to any data acquisition as it relates to setting up a model or theoretical calculations for comparison with the acquired data. In this step, calculations are made for the time delays (and thus the difference in time delays) that would be expected for pulses transmitted via the given source and receiver locations for reflections at varying depth (i.e. ROIs at varying depth) and at a reference speed of sound $c_0$.

In step 303, the difference in time delay between the two beam paths is calculated (e.g. using received signal correlation techniques). Then in step 304 the calculated difference in time delays is compared with the reference values from step 301. This may be via repeated calculations in a theoretical model or it may be via a lookup process if tabular data were generated in step 301, or any other suitable data comparison technique may be used.

Step 305 represents an optional iterative process in which the current calculated speed of sound is compared with that of the previous iteration (or a starting value if this is the first iteration). If the difference is less than a threshold value then the speed is deemed to have converged to a suitable extent and is output. The calculated speed of sound is fed back to the acquisition step 300 where it can be propagated forward through the method to be used in subsequent iterations. When a final value has been obtained, it is merged in step 306 with the other acquired data (e.g. image data) and output via a display such as a computer monitor at step 307.

It should be noted that this figure is intended to serve as an illustrative example of the implemented method, and does not necessarily represent all steps needed for practical applications of the invention. The same applies to the other figures relating to other embodiments.

IMPLEMENTATION EXAMPLE 5

FIG. 10b illustrates a minor modification to the method of FIG. 10a. The differences are firstly that in FIG. 10b, a step 308 of updating the geometry is introduced after the iteration step 305 and secondly that the output from step 308 feeds into the calculation step 301 rather than the data acquisition step 300 as it is not necessary to reacquire new data, but merely to recalculate using the revised speed of sound estimate. In addition the recordings selected for the calculations are selected from the same pulse-echo acquisition sequence, preferably comprising multiple echo signals from the same pulse. The geometry update step 308 will involve updating parameters that were dependent on the previous speed of sound estimate. For example, path lengths that were calculated from a measured time delay and the estimated speed of sound would be updated in this step.

The following description is of an implementation of a process broadly following the method of FIG. 10b and using simulated data.

This example of estimating speed of sound in a medium is illustrated with reference to FIGS. 13 to 15. The processing illustrated here uses synthetic data generated from the FIELD II Ultrasound Simulation Program.

The data were generated by using a point scatterer in a medium with a homogeneous speed of sound velocity. The transducer defined for the simulations was a linear flat array transducer with 128 elements, using plane wave imaging. The simulations were done with the point scatterer at 3 cm depth, located laterally at the midpoint of the ultrasound transducer. The synthetic data were generated by using two different values for speed of sound of the medium ($c_{om}$); 1540 m/s and 1580 m/s.

The simulated data for a single ultrasound frame for the two values of $c_{om}$ is shown in FIG. 13. It can be seen that the shortest time of flight occurs at channel number 64 directly above the point scatterer. The time of flight increases towards channel numbers 1 and 128. It can be seen that the time of flight is shorter for the case where the speed of sound is faster.

The first processing step is to correct the travel time data for geometrical differences caused by the lateral offset of the channels, keeping channel 64 (with shortest traveltime) as the reference. The one-way travel time from the scatterer to the transducer element for a given channel (element) n is given by the equation:

$$t_n = \frac{\sqrt{\Delta x_n^2 + D^2}}{c}$$

where $\Delta x_n$ is the lateral distance between the central element (element 64) and the receiver n used for the estimation, and D is the depth of the scatter (origin of the reflected echo) estimated by D=TWT*c/2, and TWT is the recorded two-way-traveltime for the element above the scatterer (here element 64).

To estimate D, a value of the speed of sound is required. This may conveniently be taken as the default speed of sound of a typical scanner which is 1540 m/s. Thus, this first correction is done using the fixed speed of sound of the scanner set to $c_{os}$=1540 m/s, and the results are seen in FIG. 14. It can be seen in this Figure that for the case where the true speed of sound is 1540 m/s, this first geometrical offset has flattened the response data out so that all transducers show approximately the same time of flight (note that the y-axis in this figure shows the geometrically corrected one-way time of flight from the scatterer to the receiver, whereas FIG. 13 showed the two-way time of flight, hence the time values being approximately halved). In the case where the true time of flight is faster (1580 m/s) than the value used for the geometrical correction (1540 m/s), the corrected times of flight are not consistent across the elements, the corrected data being curved upwards at the edges, appearing to show an earlier response at the transducer edges. This is an indication that the default value (i.e. the current estimate) of the speed of sound is inaccurate.

In the next step, the synthetic data is used as the input to the medium speed of sound calculation, using the methods described above implemented in Matlab to produce a new, improved estimate of the speed of sound.

The calculations were performed as an iterative process, and the end result after 80 iterations is illustrated in FIG. 15 in which the data is displayed with the correction of geometrical travel time differences using the final speed of sound estimate in a similar manner to FIG. 14. For the synthetic data generated with a medium speed of sound of 1540 m/s the method produced an estimated velocity of 1540.0083 m/s, while for the medium with $c_{om}$=1580 m/s the calculated velocity was 1580.1315 m/s.

In the calculations for the data illustrated in FIGS. 13-15, the difference in travel time between channels 64 and 128 was used. It will be appreciated that different pairs of channels could be used, or the comparison could be extended to compare more than two channels, e.g. all channels. It will be appreciated that in different implementations the goal of iteration could be to minimise the difference between the corrected travel times of two channels (e.g. channels 64 and 128 as above) or to minimise the spread of corrected travel times acros a number (possibly accross all) channels.

The reflected signal from a scatter for two different channels, 64 and 128, of the synthetic data is shown in FIG. 16. The three pairs of images correspond to the images of FIGS. 13-15 respectively. In each pair, the left image is for the true speed of sound of 1540 m/s and the right image is for the true speed of sound of 1580 m/s. The top images show the travel time difference due to the geometrical difference. The pulse is received at channel 64 before it is received at channel 128 due to the extra distance between the scatterer and channel 128. The middle images show the travel times adjusted to remove the geometrical difference. Here it can be seen that in the case of the true speed of sound being 1540 m/s, the pulses for channels 64 and 128 overlap almost exactly indicating that the speed of sound estimate used to calculate the geometrical correction is accurate. For the case of the true speed of sound being 1580 m/s, the pulses received at channels 64 and 128 do not overlap even after geometrical correction, thereby indicating a deviation of the speed of sound estimate from the true speed of sound. The bottom pair of images show the corrected data after the speed of sound estimate used for geometrical correction has been revised over 80 iterations. It can be seen here that the estimated speeds of sound have converged highly accurately on the true speeds of sound and that the pulses for channels 64 and 128 overlap in time with high accuracy.

In the above figures, it will be seen that the amplitude of the pulse received at channel 128 is also smaller due to the additional absorption caused by the extra distance travelled. This amplitude difference does not hinder the correlation algorithm used in this embodiment for determining the difference in time between the two pulses, although it will be appreciated that in other embodiments a normalisation step may be included to normalise the amplitudes before correlation.

In FIG. 16 the very small amplitude pulses that lag the main pulses are an artefact that is not relevant here and may be ignored.

It can be seen from the above that the results of the estimated speed of sound are very accurate for this simple case.

Figure 11A:
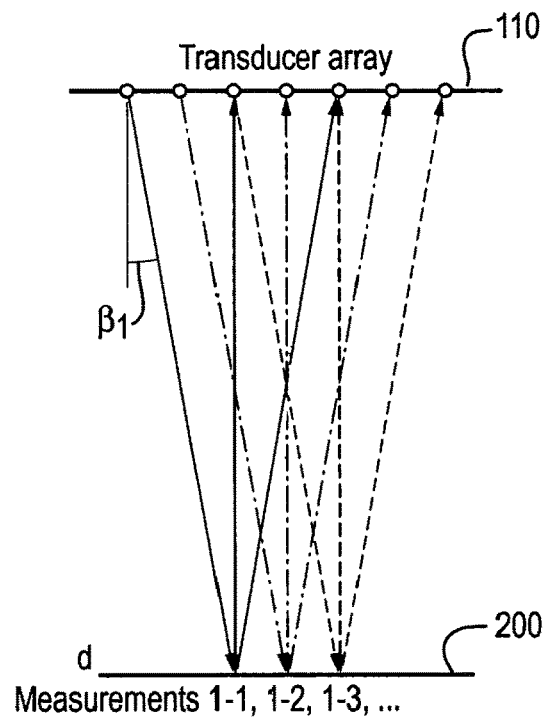
Figure 11B:
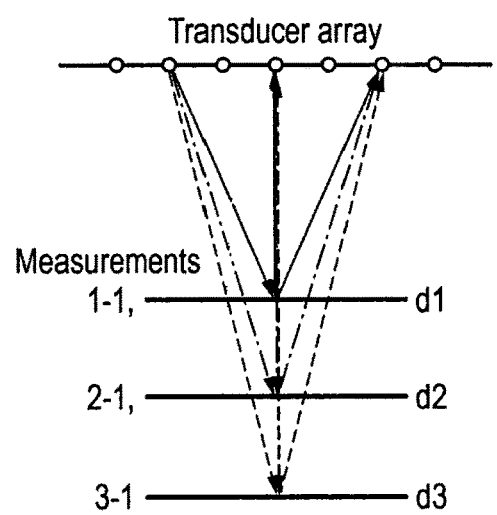

A practical implementation for finding the speed of sound for any given lateral or elevation (2D arrays) source-receiver localization could be to calculate the expected travel time difference for any travel time $t_0$ obtained for the normal incidence acoustic wave (defined as 0° beam angle), store the value in a memory buffer, estimate the true travel time difference between the zero and non-zero beam angle by e.g. a correlation based method or using a statistical based approach, divide the estimated time delay value with the observed (measured) time delay value, and multiply by the default or initial speed of sound $c_0$ used by the scanner for depth conversion. This corresponds to equation (13). This process may optionally be made iterative for improved accuracy and precision, updating the calculations with the estimated speed of sound and finding a converging speed of sound for a given ROI. The measurements for a certain ROI can be done until the speed of sound for iteration (i) is less than a certain user-defined threshold apart from the speed of sound estimated in iteration (i−1). The measurements can be repeated and performed for any given number of ROIs for any spatial position and depth by adjusting to appropriate beam angles and/or source-receiver localization as illustrated in FIG. 11. FIG. 11A shows multiple source/receiver combinations spread across the transducer array 110. Each pair of source and receiver provides a measurement (1-1, 1-2, 1-3, etc.) in the lateral direction by examining adjacent ROIs laterally along the interface 200. Each ROI is examined by at least two different beam paths, one being normal to the transducer surface and one at an angle beta1 to the transducer surface (although different beam paths at two different angles could also be used). FIG. 11B shows investigation of different depths d1, d2, d3, etc. by taking multiple measurements 1-1, 2-1, 3-1 at different depths. Each measurement comprises examination and comparison of at least two acoustic pulses sent along two different beam paths, e.g. one at normal incidence and one at an angle to the transducer surface directed at the required depth.

The estimated speed of sound represents the average speed of sound of the propagation path. The average velocity between two defined depths of a given spatial position can be calculated by subtracting the speed of sound measurement at depth d-1 from the measurement at depth d. This method therefore allows the generation of a grid in 2D and/or 3D of speed of sound measurements in space for a given medium, by repeating the measurements at the desired spatial location and regions of interest in depth. Variations in the speed of sound within an area can thus be mapped and can be used to provide more accurate measurements and calculations when imported into other measurement and image techniques. The output of the measurements can be used for internal calculations in the scanner only, exported as a data file, shown as a colour coded 2D image or 3D image volume, or any other suitable formats. The estimated speed of sound also allows calculation of distances from the transducer to objects within the investigated medium, or between objects causing echoes within the medium. The calculated distance may also be used to calculate parameters that are dependent also on distance, as amplitude decay and attenuation.

The change in travel time between the at least two signals transmitted and received may be obtained by e.g. a correlation-based method as described above, using the data received at R0 and R1 with recorded echoes from the same ROI as input for the correlation process. The correlation function can be further analysed to find the time delay between the input data for a given depth by finding the exact time (from zero lag) of the maximum magnitude of the correlation function. This may be calculated in several ways, e.g. using established methods that are known from ultrasound estimation of time delays for estimation of tissue displacement, velocity or strain using either curve fitting and interpolation of the correlation function magnitude or phase sensitive processing to obtain the exact time of the maximum. These methods may detect time delays to an accuracy within a fraction of the sampling time, in the order of nanoseconds. The correlation of the signals may be replaced by other suitable processing methods for finding the time delay, or attributes related to time delay such as e.g. phase properties, between the recorded signals.

Other embodiments of the invention may be used for estimation of curvature or the angle of interfaces within the medium.

In case of non-horizontal interfaces relative to the plane of the transducer surface in the medium explored, embodiments of the invention can be used to estimate the angle of the interface relative to the transducer surface, or relative to any other suitable reference plane.

Figure 12A:
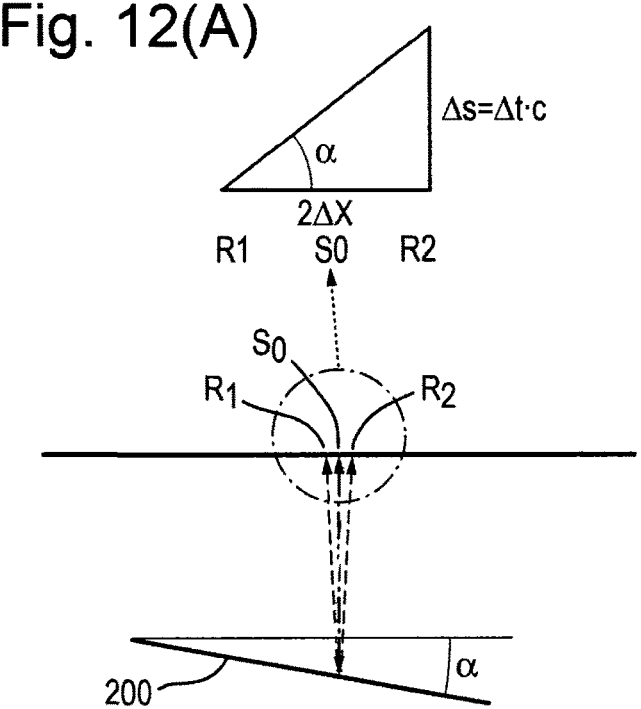
Figure 12B:
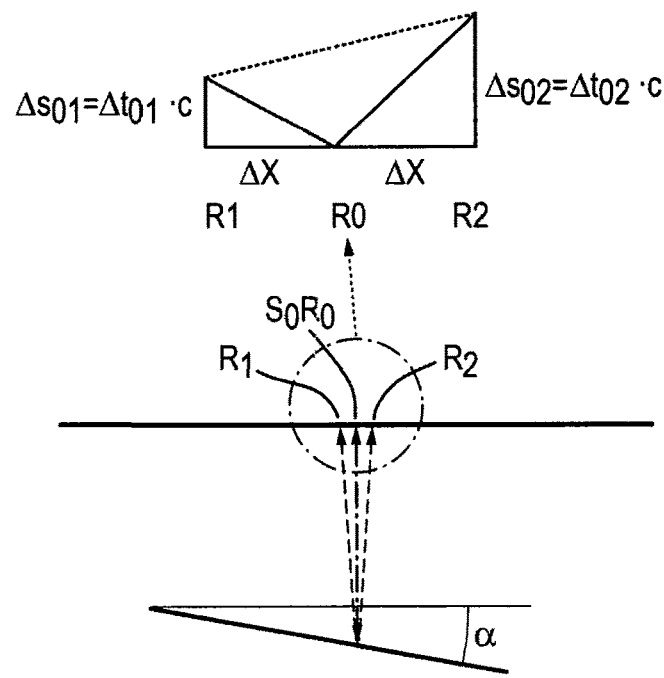

The estimates of interface curvature or angles in the medium could be obtained by emitting an acoustic pulse at a given location and beam angle, and estimating the difference in travel time for a given number of adjacent receivers. This is shown in FIG. 12. More specifically, FIG. 12A illustrates the process to estimate a dip angle for a given interface by sending a pulse from source $S_0$ and receiving on receivers $R_1$ and $R_2$. A time delay between the signals received at $R_1$ and $R_2$ can be found by for example a correlation-based method. The angle of the interface can be estimated by e.g. geometrical mathematics. FIG. 12B illustrates estimation based on sending a pulse from source $S_0$ and receiving echoes on receivers $R_0$, $R_1$ and $R_2$. The time delays between signals received at $R_0$ and $R_1$ and $R_2$ respectively are found and the angle of a given interface in the medium can be calculated by inspection of geometry, vector mathematics or other suitable methods defined by the measured time delays and the spatial distances between the receivers.

Signals transmitted from $S_0$ will be received at $R_0$, $R_1$ and $R_2$ after reflection from different locations along the boundary and therefore with different path lengths and different travel times. The difference between the travel times can be geometrically related to the inclination angle of the boundary as illustrated in the triangles depicted in the upper portion of each of FIGS. 12A and 12B. It will be appreciated that the reflections and the transmission paths need not be symmetrically arranged about the midpoint (e.g. the receivers $R_1$, $R_2$ need not be symmetrically arranged either side of $R_0$).

Based on the differences in travel times and the known distances between the source and the receiver locations, it is possible to derive the angle or curvature of an interface or body within the medium by using e.g. geometrical considerations in a similar way as has been shown in other embodiments described above.

The given approaches can be repeated for any depth and any lateral position, and thereby it is possible to track the angle of any given interface within the medium. The information about the angle of any interface can be used as input for the transmit circuit of the source, in order to steer the beams at such an angle that most of the energy of the reflected or scattered waves are projected back to the receivers or transducer. The derived curvatures of the interfaces may also be used to calculate optimal source-receiver locations for exploring the medium, i.e. estimation of positions to maximize the energy being reflected or scattered in case of curved or dipping boundary. Information about the angle of interfaces may also be used to derive better estimate of e.g. speed of sound and for generation of models (2D or 3D) for simulation or for acoustic or elastic numerical modelling. In some embodiments, the estimation of curvature of an object could be a natural part of estimating the speed of sound. Initially one can calculate the difference in travel time between received echo signals for a given ROI that is caused by the curvature of the object. Once this has been done, it is possible to derive the speed of sound accounting for the curvature of any object.

The methods of the invention is applicable for any transducer technology and geometry (1 D, 1.25D, 1.5D, 2D arrays). Where the description of angle measurements has been given above with respect to a plane to give an angle relative to that plane, it will be appreciated that a 2D array can perform the same operation relative to another plane at an angle (e.g. perpendicular) to the first plane to provide full 3D direction information for flows or particle movement or forces within the medium. The methods can also be implemented with any method of beam forming, as in conventional ultrasound where a beam is focused at a narrow point in depth, or with plane wave methods.

Embodiments of the invention may also be used for estimation of attenuation.

Embodiments of the invention can be used for analyses and quantification of attenuation or any other amplitude derived variables for any medium explored with acoustic waves. The change in amplitude of a reflected echo originating from depth Z versus the at least two different source-receiver locations or beam angles can be measured for the acoustic waves propagating in a given medium. The attenuation can be calculated as the decrease in amplitude over unit length. The spatial length can be calculated from the travel time delay between the at least two different source-receiver and/or beam angle combinations and/or propagation paths of the acoustic wave. By using Fourier transform of the time domain signal the attenuation versus frequency can be derived.

The attenuation coefficient may also be calculated by relating the measured amplitude decay as a function of source-receiver location or beam angle, and relating this decay to a similar theoretical calculated decay using a given attenuation coefficient. This approach is similar to that described above for speed of sound measurements. The attenuation coefficient of the explored medium may therefore be estimated by multiplying the attenuation coefficient used in the theoretical calculations with the fractional difference between the measured/observed and theoretically estimated amplitude decays.

It will be appreciated that the techniques above may be combined in a single apparatus. The different measurement techniques may be applied simultaneously and/or sequentially. In many cases one measurement may improve calculation for other measurements. For example, an accurately measured speed of sound (or array or map of speeds) can be used in attenuation measurements to calculate propagation lengths accurately. This combination is provided purely by way of example. Many other combinations are also possible as will be appreciated by one of ordinary skill in the art.

The invention claimed is:

1. A method of measuring a property of a medium using ultrasound, comprising:
   transmitting one or more ultrasound pulses into the medium from one or more transmitters and receiving at least a first echo signal and a second echo signal from within the medium at one or more receivers, wherein the first and second echo signals correspond to first and second pulse transmission paths within the medium from the one or more sources to the one or more receivers, the second path being different from the first path; and
   using the characteristics of the first and second echo signals together with an estimate of the property of the medium and a geometrical relationship between the first and second transmission paths to calculate a revised estimate of said property of the medium.

2. A method as claimed in claim 1, wherein the calculating step comprises:
   estimating the characteristics of the received second echo signal based on the characteristics of the received first echo signal, the estimate of the property of the medium and the geometrical relationship; and calculating the revised estimate based on the estimated characteristics of the received second echo signal and the measured characteristics of the received second echo signal.

3. A method as claimed in claim 2, wherein the characteristics of the first and second echo signals comprises the travel times of the first and second pulses respectively, and wherein the property of the medium comprises one of the following: speed of sound in the medium, attenuation in the medium.

4. A method as claimed in claim 1, wherein the calculating step comprises:
estimating a feature of the second path based on the estimate of the property of the medium, the characteristics of the received first echo signal and the geometrical relationship;
estimating the same feature of the second path based on the estimate of the property of the medium and the characteristics of the received second echo signal; and
calculating the revised estimate based on a comparison of the two estimates of the feature of the second path.

5. A method as claimed in claim 4, wherein the feature of the second path is the path length of the second path and wherein the property of the medium comprises one of the following: speed of sound in the medium, attenuation in the medium.

6. A method as claimed in claim 1, wherein the characteristics of the first and second echo signals used in the calculations include one or more of: travel time, received amplitude, received phase, frequency spectrum, or any characteristic derived from the above mentioned characteristics.

7. A method as claimed in claim 1, wherein the medium properties calculated from the echo signal characteristics include one or more of: speed of sound in the medium, attenuation in the medium, flow or particle movement direction within the medium, displacement within the medium, strain within the medium, velocities within the medium, and angle or curvature of interfaces or bodies within the medium, or any properties derived from any of the previously stated properties.

8. A method as claimed in claim 1, wherein the speed of sound in the medium is calculated from the difference in travel times along each of the first and second paths and the distances between source and receiver for each of the first and second paths.

9. A method as claimed in claim 1, wherein the speed of sound in the medium is calculated from the difference in travel times along each of the first and second paths and the beam angles for each of the first and second paths.

10. A method as claimed in claim 1, wherein the attenuation in the medium is calculated based on the received amplitudes of the first and second echo signals and the path lengths of the first and second transmission paths.

11. A method as claimed in claim 1, wherein a flow or particle movement direction within the medium and/or magnitude is calculated based on the angle between the two transmit directions and the velocities measured along the two paths.

12. A method as claimed in claim 1, wherein the inclination angle of a boundary within the medium with respect to the transducer surface is calculated based on the difference in travel times along each of the first and second paths and the distances between source and receiver for each path.

13. A method as claimed in claim 1, further comprising comparing the received echo signal characteristics with outputs from a theoretical model that models the medium so as to extract or calculate the model parameters that best match the received echo characteristics.

14. A method as claimed in claim 13, wherein the model provides expected time differences for a given reference speed of sound at various depths and various source locations and receiver locations.

15. An ultrasound apparatus for measuring a property of a medium, comprising:
one or more sources for transmitting ultrasound pulses into the medium;
one or more receivers for receiving ultrasound pulses from the medium; and
a processor configured and operable to:
transmit one or more ultrasound pulses into the medium and receive at least first and second echo signals from within the medium, wherein the first and second echo signals correspond to first and second pulse transmission paths within the medium from the at least one source to the at least one receiver, the second path being different from the first path; and
use the characteristics of the first and second echo signals together with an estimate of the property of the medium and a geometrical relationship between the first and second transmission paths to calculate a revised estimate of said property of the medium.

16. An apparatus as claimed in claim 15, wherein the processor is configured and operable to:
estimate the characteristics of the received second echo signal based on the characteristics of the received first echo signal, the estimate of the property of the medium and the geometrical relationship; and
calculate the revised estimate based on the estimated characteristics of the received second echo signal and the measured characteristics of the received second echo signal.

17. An apparatus as claimed in claim 16, wherein the characteristics of the first and second echo signals comprises the travel times of the first and second pulses respectively, and wherein the property of the medium comprises one of the following: speed of sound in the medium, attenuation in the medium.

18. An apparatus as claimed in claim 15, wherein the processor is configured and operable to:
estimate a feature of the second path based on the estimate of the property of the medium, the characteristics of the received first echo signal and the geometrical relationship;
estimate the same feature of the second path based on the estimate of the property of the medium and the characteristics of the received second echo signal; and
calculate the revised estimate based on a comparison of the two estimates of the feature of the second path.

19. An apparatus as claimed in claim 18, wherein the feature of the second path is the path length of the second path and wherein the property of the medium comprises one of the following: speed of sound in the medium, attenuation in the medium.

20. An apparatus as claimed in claim 15, wherein the echo signal characteristics used in calculations include one or more of: travel time, received amplitude, received phase, frequency spectrum, or any characteristic derived from the above mentioned characteristics.

21. An apparatus as claimed in claim 15, wherein the processor is configured and operable to calculate one or more of: speed of sound in the medium, attenuation in the medium, flow or particle movement direction within the medium, displacement within the medium, strain within the medium, velocities within the medium, and angle or curvature of interfaces or bodies within the medium, or any properties derived from any of the previously stated properties.

22. An apparatus as claimed in claim 15, wherein the processor is configured and operable to calculate the speed of sound in the medium from the difference in travel times along each of the first and second paths and the distances between source and receiver for each of the first and second paths.

23. An apparatus as claimed in claim 15, wherein the processor is configured and operable to calculate the speed of sound in the medium from the difference in travel times along each of the first and second paths and the beam angles for each of the first and second paths.

24. An apparatus as claimed in claim 15, wherein the processor is configured and operable to calculate a flow or particle movement direction within the medium and/or magnitude based on the angle between the two transmit directions and the velocities measured along the two paths.

* * * * *